(12) United States Patent
Porte et al.

(10) Patent No.: US 7,550,629 B2
(45) Date of Patent: Jun. 23, 2009

(54) TRIFLUOROMETHYL-CONTAINING PHENYLSULFONAMIDE BETA AMYLOID INHIBITORS

(75) Inventors: Alexander Michael Porte, Pennington, NJ (US); Thomas Joseph Caggiano, Morrisville, PA (US); George Diamantidis, Randolph, NJ (US); Diane Barbara Hauze, Radnor, PA (US); Boyd Lynn Harrison, Princeton Junction, NJ (US); Molly Hoke, Hightstown, NJ (US); Anthony Kreft, Langhorne, PA (US); Dennis M. Kubrak, Philadelphia, PA (US); Charles William Mann, Philadelphia, PA (US); Scott Mayer, Bridgewater, NJ (US); Koi Michele Morris, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/788,349

(22) Filed: Apr. 19, 2007

(65) Prior Publication Data

US 2007/0249722 A1 Oct. 25, 2007

Related U.S. Application Data

(60) Provisional application No. 60/793,852, filed on Apr. 21, 2006.

(51) Int. Cl.
C07C 311/01 (2006.01)
C07C 307/00 (2006.01)
(52) U.S. Cl. .......................... 564/80; 564/86
(58) Field of Classification Search ................ 564/80, 564/86, 393, 489; 514/361; 562/439
See application file for complete search history.

(56) References Cited

U.S. PATENT DOCUMENTS

| 6,610,734 | B2 | 8/2003 | Kreft et al. | |
|---|---|---|---|---|
| 6,657,070 | B2 | 12/2003 | Resnick | |
| 6,878,742 | B2 | 4/2005 | Kreft et al. | |
| 7,166,622 | B2 * | 1/2007 | Kreft et al. | 514/361 |
| 2004/0198778 | A1 | 10/2004 | Kreft et al. | |
| 2005/0171180 | A1 | 8/2005 | Resnick et al. | |
| 2005/0196813 | A1 | 9/2005 | Kreft et al. | |
| 2007/0197800 | A1 * | 8/2007 | Chan et al. | 549/62 |

FOREIGN PATENT DOCUMENTS

WO   WO-03/103660   12/2003
WO   WO-2004/092155   10/2004

OTHER PUBLICATIONS

Umemoto et al., "Synthesis, Properties, and Reactivity of (1H,1H-Perfluoroalkyl) and (1H-Perfluoro-1-alkenyl)aryliodonium Triflates and Their Analogs", Bull. Chem. Soc. Jpn., 60:3307-3313 (Sep. 1987).

Umemoto et al., "1H,1H-Perfluoroalkylation of Enol Silyl Ethers with (1H,1H-Perfluoroalkyl)phenyliodonium Triflates. A New Method for the Preparation of β- and σ- Trifluoromethyl Carbonyl Compounds and Their Higher Perfluoroalkyl Homologues", Bull. Chem. Soc. Jpn., 60:3823-3825 (Oct. 1987).

Evans et al., "Electrophilic Azide Transfer to Chiral Enolates. A General Approach to the Asymmetric Synthesis of α-Amino Acids", J. Am. Chem. Soc., 109:6881-6883 (1987).

Davis et al., "Asymmetric Strecker Synthesis Using Enantiopure Sulfinimines and Diethylaluminum Cyanide: The Alcohol Effect", J. Org. Chem., 61(2):440-441, Jan. 26, 1996.

Enders et al., "Enantioselective Synthesis of 3-Substituted 2-Ketoesters", Angew. Chem. Int. Ed. Engl., 31(5):618-620, 1992.

Enders et al., "Enantioselective Synthesis of Protected Isotetronic Acids", Chem. Eur. J., 4(2):311-320, 1998.

Han et al., "Total Asymmetric Synthesis of Highly Constrained Amino Acids β-Isopropyl-2',6'-Dimethyl-Tyrosines", Tetrahedron Letters, 38(29):5135-5138, 1997.

Speelman et al., "Molecular Structure of a Chiral 3,5-Bridged Pyridine and the Effect of Structure on Circular Dichoric Spectra", J. Org. Chem., 54:1055-1062, 1989.

Alimardanov, "Practical Asymmetric Synthesis of Trifluoromethyl-Containing Aminoester Using a Modified Davis Protocol", Organic Process Research & Development, 12:424-428 (Epub: May 1, 2008).

Zhang, "Asymmetric Synthesis of Novel α-amino Acids With β-branched Side Chains", Bioorganic & Medicinal Chemistry Letters, 17(9):2401-2403 (May 1, 2007 Epub: Feb. 17, 2007).

Kreft, "Discovery of a Novel Series of Notch-Sparing γ-Secretase Inhibitors" Bioorganic & Medicinal Chemistry Letters, 18(14):4232-4236 (Jul. 15, 2008 EPub: May 20, 2008).

* cited by examiner

*Primary Examiner*—Rosalynd Keys
*Assistant Examiner*—Yate' K Cutliff
(74) *Attorney, Agent, or Firm*—Scott K. Larsen; Howson & Howson LLP

(57) ABSTRACT

A compound of Formula (I), or pharmaceutically acceptable salts and/or hydrates or prodrugs thereof, wherein Formula (I) has the structure:

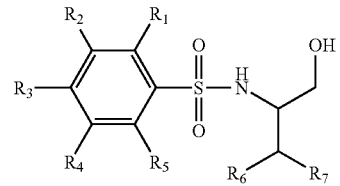

is provided, wherein $R_1$-$R_7$ are defined herein. These compounds are useful in medicaments for treating a disease selected from the group consisting of Alzheimer's Disease, amyloid angiopathy, cerebral amyloid angiopathy, systemic amyloidosis, hereditary cerebral hemorrhage with amyloidosis of the Dutch type, inclusion body myositis, mild cognitive impairment (MCI) and Down's syndrome, in a subject.

13 Claims, No Drawings

TRIFLUOROMETHYL-CONTAINING PHENYLSULFONAMIDE BETA AMYLOID INHIBITORS

CROSS-REFERENCE TO RELATED APPLICATIONS

This application claims the benefit of the priority of U.S. Provisional Patent Application No. 60/793,852, filed Apr. 21, 2006.

BACKGROUND OF THE INVENTION

This invention relates to inhibitors of beta amyloid production, which have utility in the treatment of Alzheimer's disease.

Alzheimer's Disease (AD) is the most common form of dementia (loss of memory) in the elderly. The main pathological lesions of AD found in the brain consist of extracellular deposits of beta amyloid protein in the form of plaques and angiopathy and intracellular neurofibrillary tangles of aggregated hyperphosphorylated tau protein. Recent evidence has revealed that elevated beta amyloid levels in the brain not only precede tau pathology but also correlate with cognitive decline. Further suggesting a causative role for beta amyloid in AD, recent studies have shown that aggregated beta amyloid is toxic to neurons in cell culture.

Beta amyloid protein is composed mainly of 39-42 amino acid peptides and is produced from a larger precursor protein called amyloid precursor protein (APP) by the sequential action of the proteases beta and gamma secretase. Although rare, cases of early onset AD have been attributed to genetic mutations in APP that lead to an overproduction of either total beta amyloid protein or its more aggregation-prone 42 amino acid isoform. Furthermore, people with Down's Syndrome possess an extra chromosome that contains the gene that encodes APP and thus have elevated beta amyloid levels and invariably develop AD later in life.

Heterocyclic sulfonamide inhibitors of beta amyloid production have been described. U.S. Pat. No. 6,878,742 (2005) and U.S. Pat. No. 6,610,734 (2003). Fluoro-and trifluoroalkyl-containing heterocyclic sulfonamide inhibitors of beta amyloid production have also been described in U.S. Patent Application Publication No. US2004/0198778.

There continues to be a need for compositions useful in inhibiting beta amyloid production and in the treatment of the effects of Alzheimer's Disease (AD).

SUMMARY OF THE INVENTION

In one aspect, a compound of Formula (I), or pharmaceutically acceptable salts and/or hydrates or prodrugs thereof, is provided wherein Formula (I) has the structure:

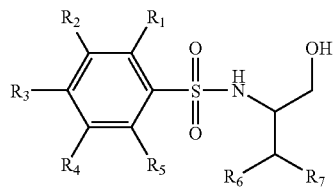

wherein $R_1$ through $R_7$ are defined herein.

In another aspect, a pharmaceutical composition is provided which contains a compound described herein and a physiologically compatible carrier.

In yet a further aspect, a method of inhibiting beta amyloid production in a subject is provided by delivering a compound or composition described herein.

In still a further aspect, a method of treating a disease selected from among Alzheimer's Disease, amyloid angiopathy, cerebral amyloid angiopathy, systemic amyloidosis, hereditary cerebral hemorrhage with amyloidosis of the Dutch type, inclusion body myositis, mild cognitive impairment (MCI) and Down's syndrome is provided.

Other aspects and advantages of the invention will be apparent from the following detailed description of the invention.

DETAILED DESCRIPTION OF THE INVENTION

Compounds of formula (I), their pharmaceutical formulations, and their use in inhibiting beta amyloid production in patients susceptible to, or suffering from, AD or other diseases resulting from elevated levels of beta amyloid protein in the brain are described. The compounds of formula (I) include pharmaceutically acceptable salts and/or hydrates or prodrugs thereof, wherein:

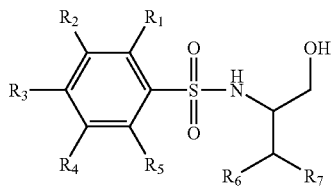

wherein, $R_1$ through $R_5$ are independently selected from H, halogen, lower alkyl, lower alkoxy, $OCF_3$, $OCF_2H$, $CF_3$, $NO_2$, CN, $CH_3CO$, and $SCH_3$; $R_6$ and $R_7$ are independently selected from lower alkyl and $CF_3(CH_2)_n$; n is independently selected from 0, 1, 2 and 3, provided that at least one of $R_6$ and $R_7$ are $CF_3(CH_2)_n$.

In one embodiment, $R_1$, $R_2$, $R_4$, and $R_5$ are H; $R_3$ is halogen, $R_6$ and $R_7$ are $CF_3$ with S-stereochemistry at the chiral center.

The term "alkyl" is used herein to refer to both straight- and branched-chain saturated aliphatic hydrocarbon groups having one to ten carbon atoms (e.g., $C_1$, $C_2$, $C_3$, $C_4$, $C_5$, $C_6$, $C_7$, $C_8$, $C_9$, or $C_{10}$), such as one to eight carbon atoms (e.g., $C_1$, $C_2$, $C_3$, $C_4$, $C_5$, $C_6$, $C_7$, or $C_8$), one to six carbon atoms (e.g., $C_1$, $C_2$, $C_3$, $C_4$, $C_5$, or $C_6$), or one to four carbon atoms (e.g., $C_1$, $C_2$, $C_3$, or $C_4$). The term "lower alkyl" refers to straight- and branched-chain saturated aliphatic hydrocarbon groups having one to six carbon atoms (e.g., $C_1$, $C_2$, $C_3$, $C_4$, $C_5$, or $C_6$), desirably one to four carbon atoms (e.g., $C_1$, $C_2$, $C_3$, or $C_4$).

The term "alkoxy" is used herein to refer to the O(alkyl) group, where the point of attachment is through the oxygen-atom and the alkyl can be optionally substituted.

The term "halogen" refers to Cl, Br, F, or I.

The pharmaceutically acceptable salts are those derived from such organic and inorganic bases as: sodium hydroxide, potassium hydroxide, calcium hydroxide, magnesium hydroxide, diethanolamine, ethylenediamine and similarly known acceptable bases. Prodrugs of the compounds may be produced and utilized by one skilled in the art.

Synthesis

The compounds can be prepared in a number of ways well known to one skilled in the art of organic synthesis. More particularly, the compounds can be prepared using the methods described below, together with synthetic methods known in the synthetic organic arts or variations of these methods by one skilled in the art. Desirable methods include, but are not limited to, those outlined below.

A first method of preparation includes reaction of a 1,2-amino alcohol II with the appropriate sulfonyl halide in the presence of a base, such as triethylamine, in a suitable solvent to afford compounds of formula I (Scheme 1).

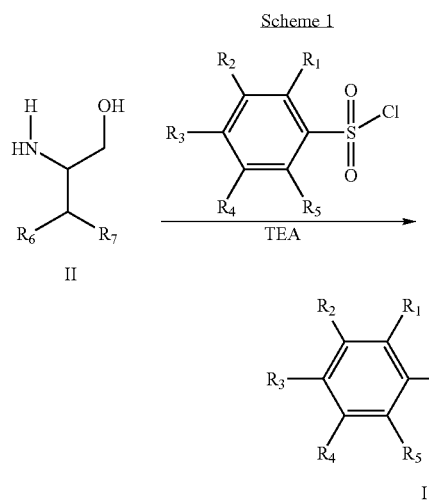

A second method of preparation involves reaction of an α-amino acid or ester III with the appropriate sulfonyl halide in the presence of a base, such as triethylamine, in a suitable solvent to afford compounds of formula IV (Scheme 2). The intermediate N-sulfonyl acid IV (Rx=H) can be converted to the corresponding primary alcohol I utilizing standard methodology such as LiAlH$_4$, B$_2$H$_6$ or cyanuric chloride/NaBH$_4$. The intermediate N-sulfonyl ester IV (Rx=alkyl, Bn) can also be reduced to the corresponding primary alcohol I utilizing standard methodology such as LiAlH$_4$.

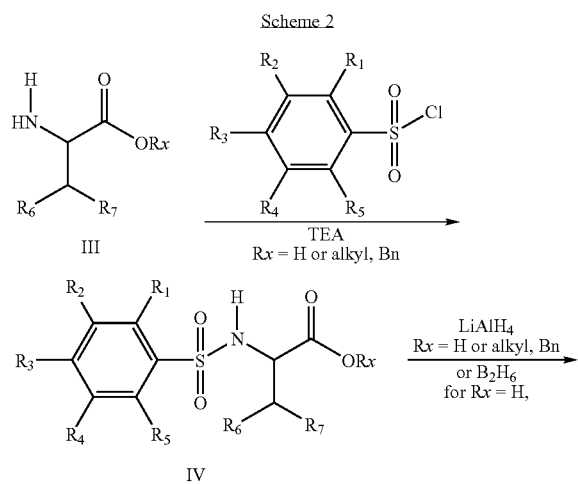

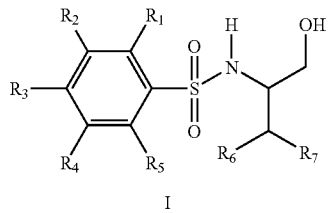

In a variation of the second method to prepare the primary alcohols, an α-amino acid or ester (or N-protected derivative thereof) V is first converted to the corresponding primary 1,2-aminoalcohol VI (using the methodology outlined in Scheme 2), which is subsequently, after deprotection (if necessary), reacted with the appropriate sulfonyl halide (Scheme 3) to afford compounds of formula I.

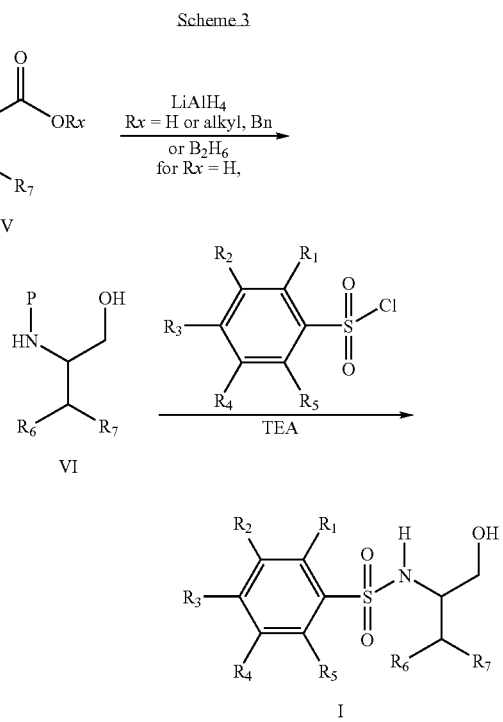

P = protecting group

For preparation of compounds derived from unnatural α-amino acids containing beta branching in the amino acid side chain, a method of preparation based on the work of Hruby (Tet. Lett. 38: 5135-5138 (1997)) is outlined in Scheme 4. This route entails formation of the α,β-unsaturated amide X of an Evans chiral auxiliary from bromoacetyl bromide VII via a Horner-Emmons reaction sequence, followed by conjugate addition of an organocuprate, trapping of the resulting enolate anion XI with NBS, displacement of bromide XII with azide anion to afford XIII, followed by reduction to the 1,2-amino alcohol and subsequent sulfonylation to afford the target compound XIV.

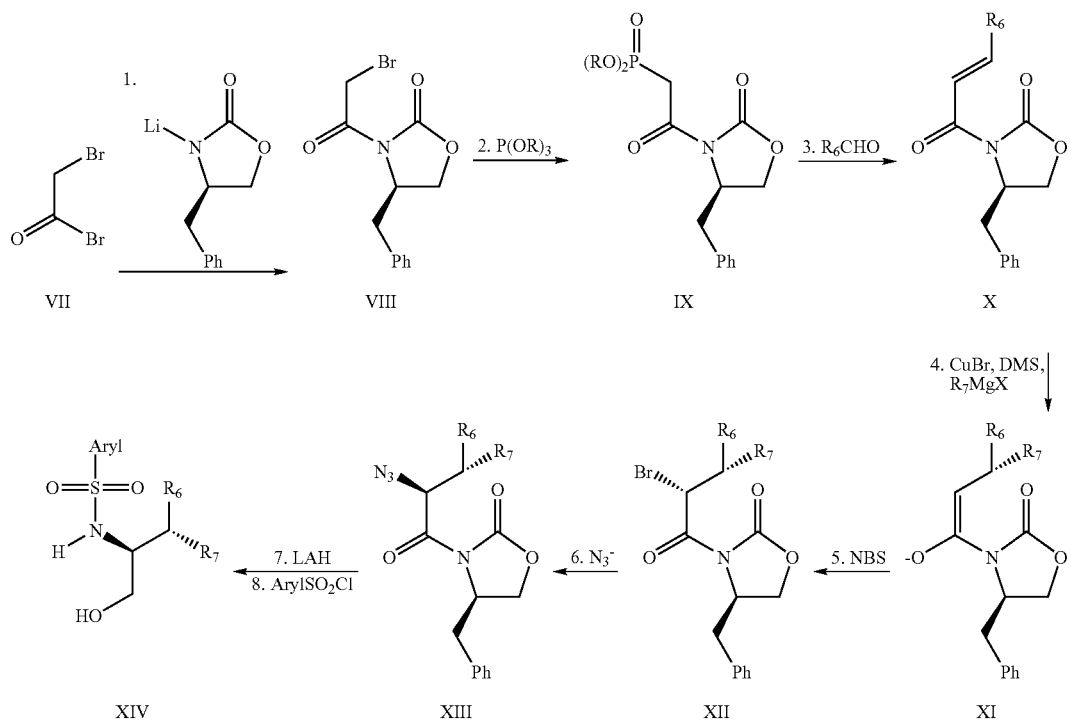

Scheme 4

An alternate preparation of sulfonamides derived from unnatural 1,2-amino alcohols utilizes the Bucherer modification of the Strecker α-amino acid synthesis (Scheme 5). In this route, an aldehyde XV is reacted with cyanide anion and ammonium carbonate to afford the hydantoin XVI which is hydrolyzed to the α-amino acid XVII. This compound is then reduced to XVIII and sulfonylated to afford the desired compounds of formula XIX. Alternatively the intermediate amino acid XVII can be first sulfonylated to afford XX, which is then reduced to XIX. The racemic products XVI, XVII, XVIII, XIX or XX can be resolved to the desired S enantiomer using standard methodology by one skilled in the art.

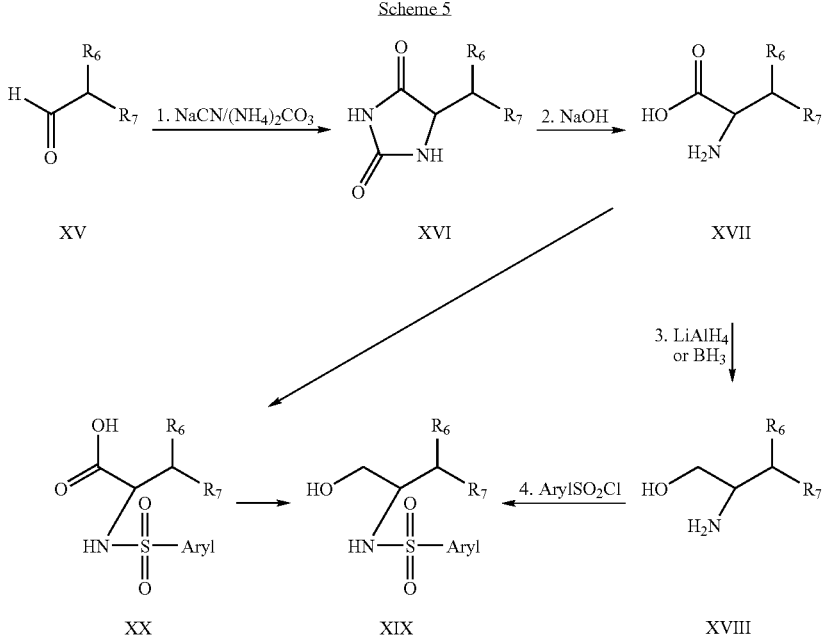

Scheme 5

Another method of preparing chirally pure N-sulfonyl 1,2-amino alcohols derived from α-amino acids is outlined in Scheme 6. This method initially involves formation of the α,β-unsaturated amide XXIII of the Evans chiral auxiliary from bromoacetyl bromide VII via a Horner-Emmons reaction sequence. Conjugate addition of an organocuprate and protonation of the resulting enolate anion affords XXIV, which is then converted to the corresponding enolate and electrophilically aminated with trisyl azide to afford the key intermediate XXV (J. Am. Chem. Soc. 109: 6881-6883 (1987)). The azide intermediate XXV is then hydrolyzed to the α-azido acid XXVI and reduced to the chirally pure α-amino acid XXVII which can be converted to the corresponding N-sulfonyl 1,2-amino alcohols by methods previously described above (e.g., Scheme 2).

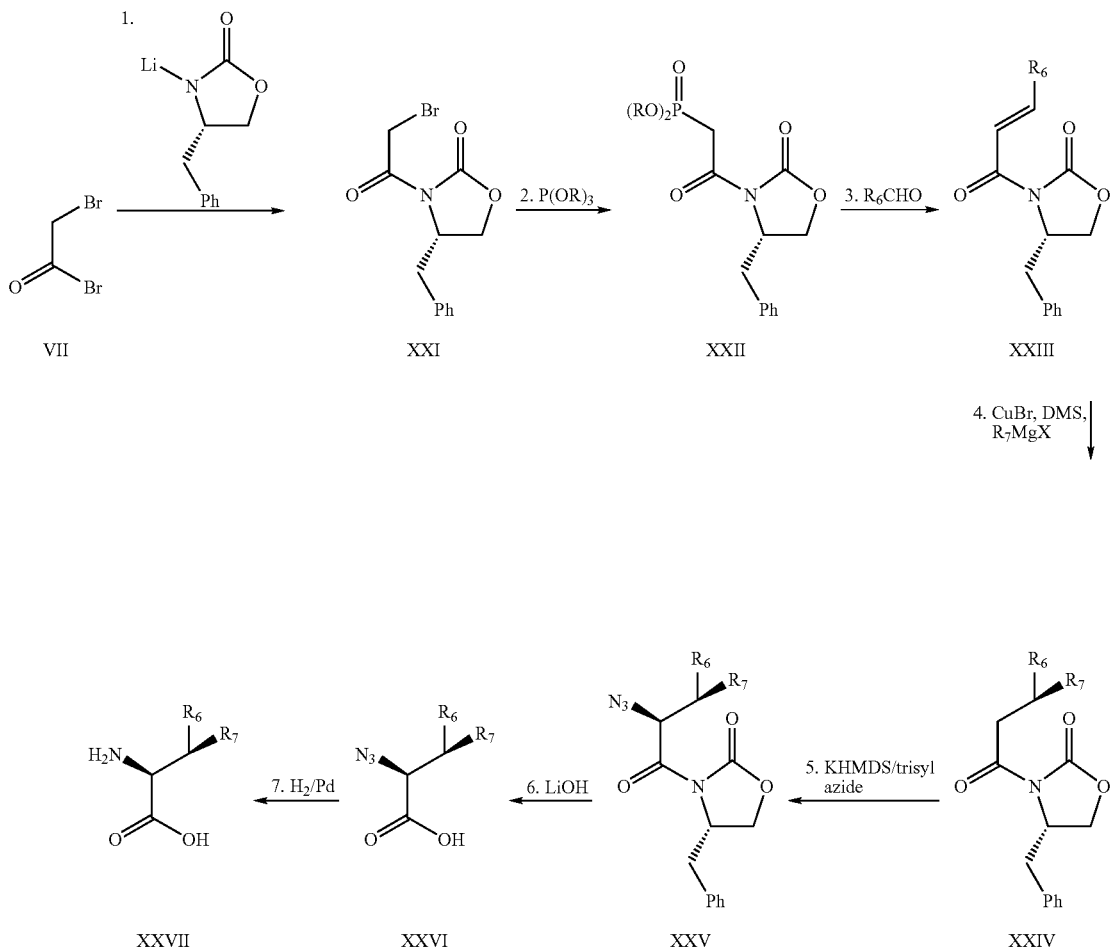

Finally, chirally pure α-amino acids XXX, one of the possible synthetic precursors of chiral N-sulfonyl 2-amino alcohols XXXII, can also be prepared utilizing asymmetric variants of the Strecker α-amino acid synthesis as outlined in Scheme 7 (J. Org. Chem. 61:440-441 (1996)) and Scheme 8 (J. Org. Chem. 54:1055-1062 (1989)).

are described in U.S. Provisional Patent Application No. 60/793,874, filed Apr. 21, 2006. The methods described in these applications are hereby incorporated by reference and may be adapted for use as described herein.

Pharmaceutical Formulation

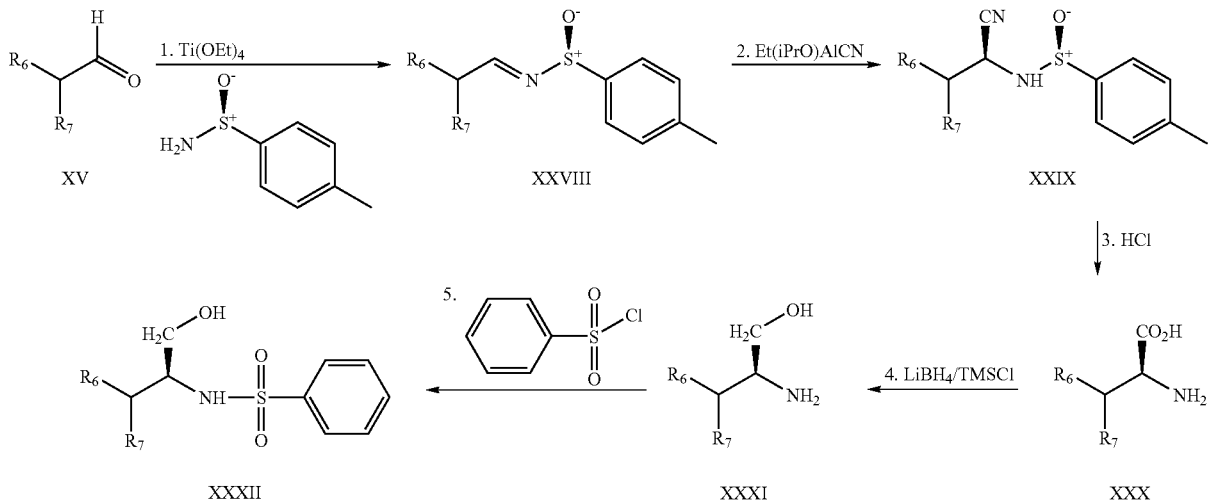

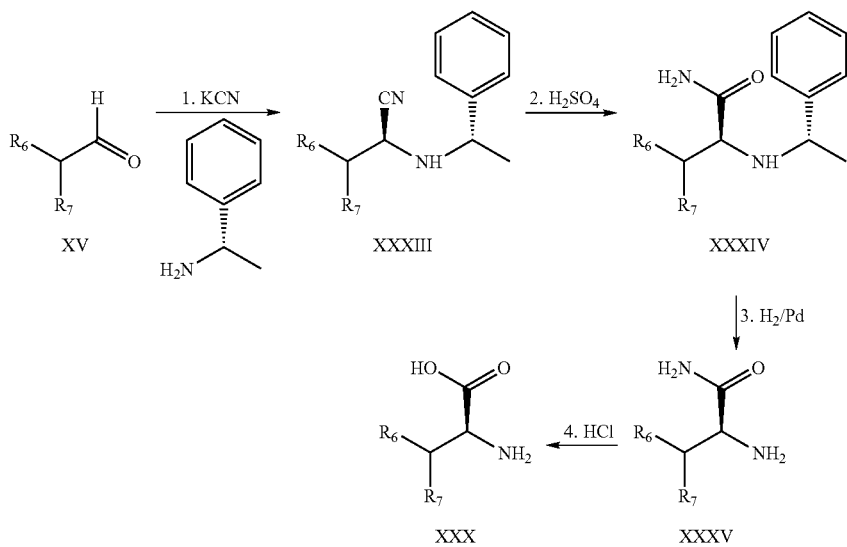

Still other suitable methods may be selected by one of skill in the art. For example, another suitable method for selectively N-sulfonylation of 2-amino trifluoroalkyl substituted alcohols has been described in the co-owned U.S. Provisional Patent Application No. 60/774,300, filed Feb. 17, 2006. Methods for preparing sulfonamide substituted alcohols and intermediates thereof are described in co-owned U.S. Provisional Patent Application No. 60/774,453, also filed Feb. 17, 2006. Further, methods for production of chirally pure amino alcohol intermediates, derivatives thereof, and uses thereof The compounds may be administered to a subject by any desirable route, taking into consideration the specific condition for which it has been selected. By subject is meant any suitable mammal, including humans, domestic animals (e.g., canines and felines), and livestock, which have been recognized as having or at risk of having one or more of the conditions for which modulation of beta amyloid levels is desirable. Thus, the compounds are useful for treatment and/ or prevention of a number of human and veterinary conditions. As used herein, "prevention" encompasses prevention of symptoms in a subject who has been identified as at risk for the condition, but has not yet been diagnosed with the same and/or who has not yet presented any symptoms thereof.

These compounds may be delivered or administered by any suitable route of delivery, e.g., oral, intravenous, subcutaneous, intramuscular, sublingual, intracranial, epidural, intratracheal, rectal (suppository), vaginal, among others. Most desirably, the compounds are delivered orally or by a suitable parenteral route. The compounds may be formulated in combination with conventional pharmaceutical carriers that are physiologically compatible. Optionally, one or more of the compounds may be mixed with other active agents.

Suitable physiologically compatible carriers may be readily selected by one of skill in the art. For example, suitable solid carriers include, among others, one or more substances which may also act as lubricants, solubilizers, suspending agents, fillers, glidants, compression aids, binders or tablet-disintegrating agents or an encapsulating material. In powders, the carrier is a finely divided solid, which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, starch, sugars (including, e.g., lactose and sucrose), dicalcium phosphate, cellulose (including, e.g., microcrystalline cellulose, methyl cellulose, sodium carboxymethyl cellulose), and kaolin.

Liquid carriers may be used in preparing solutions, suspensions, emulsions, syrups and elixirs. The active ingredient can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, suspending agents, thickening agents, viscosity regulators, stabilizers or osmoregulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols, e.g., glycols) and their derivatives, and oils (e.g., fractionated coconut oil, arachis oil, corn oil, peanut oil, and sesame oil). For parenteral administration the carrier can also be an oily ester such as ethyl oleate and isopropyl myristate. Sterile liquid carriers are used in sterile liquid form compositions for parenteral administration.

Optionally, additives customarily employed in the preparation of pharmaceutical compositions may be included in the compositions. Such components include, e.g., sweeteners or other flavoring agents, coloring agents, preservatives, and antioxidants, e.g., vitamin E, ascorbic acid, BHT and BHA.

Liquid pharmaceutical compositions that are sterile solutions or suspensions can be utilized by, for example, intramuscular, intraperitoneal or subcutaneous injection. Sterile solutions can also be administered intravenously. Oral administration may be either liquid or solid composition form.

Desirably, the pharmaceutical composition is in unit dosage form, e.g. as tablets or capsules. In such form, the composition is sub-divided in unit dose containing appropriate quantities of the active ingredient. Te unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

As described herein, a therapeutically or prophylactically useful amount of a compound is that amount of a compound which alleviates the symptoms of the disease, e.g., AD, or which prevents the onset of symptoms, or the onset of more severe symptoms. Generally, an individual dose (i.e., per unit, e.g., tablet) of a compound may be in the range from about 1 µg/kg to about 10 g/kg. In one example, an individual dose of a compound is 10 mg/kg to about 5 g/kg. In another example, an individual dose of a compound is about 1 mg/kg to about 200 mg/kg. Desirably, these amounts are provided on a daily basis. However, the dosage to be used in the treatment or prevention of a specific cognitive deficit or other condition may be subjectively determined by the attending physician. The variables involved include the specific cognitive deficit and the size, age and response pattern of the patient. For example, based upon the activity profile and potency of the compounds, a starting dose of about 10 mg per day with gradual increase in the daily dose to about 200 mg per day may provide the desired dosage level in the human.

Alternatively, the use of sustained delivery devices may be desirable, in order to avoid the necessity for the patient to take medications on a daily basis. "Sustained delivery" is defined as delaying the release of an active agent, i.e., a compound described herein, until after placement in a delivery environment, followed by a sustained release of the agent at a later time. Those of skill in the art know suitable sustained delivery devices. Examples of suitable sustained delivery devices include, e.g., hydrogels (see, e.g., U.S. Pat. Nos. 5,266,325; 4,959,217; and 5,292,515), an osmotic pump, such as described by Alza (U.S. Pat. No. 4,295,987 and U.S. Pat. No. 5,273,752) or Merck (European Patent No. 314,206), among others; hydrophobic membrane materials, such as ethylenemethacrylate (EMA) and ethylenevinylacetate (EVA); bioresorbable polymer systems (see, e.g., International Patent Publication No. WO 98/44964, Bioxid and Cellomeda; U.S. Pat. No. 5,756,127 and U.S. Pat. No. 5,854,388); other bioresorbable implant devices have been described as being composed of, for example, polyesters, polyanhydrides, or lactic acid/glycolic acid copolymers (see, e.g., U.S. Pat. No. 5,817, 343 (Alkermes Inc.)). For use in such sustained delivery devices, the compounds may be formulated as described herein.

The compounds and compositions may also be packaged in a suitable container for storage, shipment, and/or in the form a kit of parts containing the compound and/or packaging.

EXAMPLES

The following examples are provided to illustrate the production and activity of representative compounds and to illustrate their performance in a screening assay. One skilled in the art will appreciate that although specific reagents and conditions are outlined in the following examples, these reagents and conditions are not a limitation on the present invention.

Example 1

4-Chloro-N-[(1S)-3,3,3-trifluoro-1-(hydroxymethyl)-2-(trifluoromethyl)propyl]benzenesulfonamide

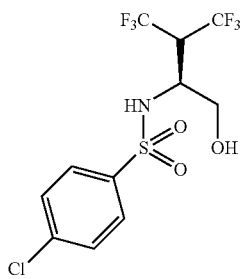

Method One

A. Methyl 2-amino-3-(trifluoromethyl)-4,4,4-trifluorobutanoate

A solution of 4,4,4,4',4',4'-hexafluoro-dl-valine (2.00 g, 8.89 mmol) in $CH_2Cl_2$:MeOH (4:1, 50 mL) was stirred under nitrogen at 0° C. TMS diazomethane (5.33 mL, 2.0 M in hexane) was added dropwise and the resulting solution stirred for 4 hours at 25° C. After this time period, the reaction was complete by TLC (10% MeOH: chloroform). After concentration, the resulting residue (2.12 g, 99%) was used directly in the next reaction without further purification.

B. Methyl 2-[(4-chloro-phenyl)sulfonylamino]-3-trifluoromethyl-4,4,4-trifluorobutanoate A solution of methyl 2-amino-3-(trifluoromethyl)-4,4,4-trifluorobutanoate (2.12 g, 8.87 mmol) in $CH_2Cl_2$ (10 mL) was stirred under nitrogen at 25° C. Pyridine (10 mL, 126 mmol) was added dropwise followed by 4-chloro-benzenesulfonyl chloride (2.81 g, 13.3 mmol) in one portion, and the resulting solution stirred for 18 hours at 25° C. After this time period, the reaction was complete by TLC (20:80 EtOAc:PE). After quenching with $H_2O$, the mixture was diluted with $Et_2O$ (200 mL). The organic layer was washed with 1 N aq. HCl (20 mL), sat. aq. $NaHCO_3$ (20 mL), and brine (20 mL), and then dried ($MgSO_4$). After concentration, the crude product was purified by Biotage Flash™ 40 chromatography, eluent: 5:95 to 20:80 EtOAc:PE, to obtain methyl 2-[(4-chloro-phenyl)sulfonylamino]-3-trifluoromethyl-4,4,4-trifluorobutanoate as a solid (1.53 g, 42%). Mass Spectrum (−ESI): 414 $[M-H]^-$.

C. 4-Chloro-N-[(1S)-3,3,3-trifluoro-1-(hydroxymethyl)-2-(trifluoromethyl)propyl]benzenesulfonamide A solution of LAH (0.140 g, 3.70 mmol) in $Et_2O$ (17 mL) was stirred under nitrogen at 0° C. To this mixture was added dropwise methyl 2-[(4-chloro-phenyl)sulfonylamino]-3-trifluoromethyl-4,4,4-trifluorobutanoate (1.53 g, 3.70 mmol) in $Et_2O$ (3 mL). After stirring at this temperature for 0.5 h, the reaction was complete by TLC (30:70 EtOAc:PE). This mixture (with efficient stirring) was quenched with the dropwise addition of $H_2O$ (0.140 mL), 15% aq. NaOH (0.140 mL), and $H_2O$ (0.420 mL) and then stirred an additional 2 hours at 25° C. The resulting slurry was dried ($Na_2SO_4$) and then filtered. After concentration, the crude product was purified by Biotage Flash™ 40 chromatography, eluent: 5:95 to 30:70 EtOAc:PE, to obtain 4-chloro-N-[(3,3,3-trifluoro-1-(hydroxymethyl)-2-(trifluoromethyl)propyl]benzenesulfonamide as a solid (0.657 g, 46%, racemic mixture). The title compound (0.277 g) was then isolated as an off-white solid using chiral HPLC [Chiralcel® AS column; 2×25 cm, 240 nm, 0.75 mL injections; mobile phase: 12 mL/min 10% IPA in hexane/0.1% TFA (premix); product is peak two, $R_f$=13.9, >99% purity]. Mass Spectrum (−ESI): 383.98 $[M-H]^-$.

Anal. Calc'd for $C_{11}H_{10}ClF_6NO_3S$: C, 34.25; H, 2.61; N, 3.63; Found: C, 34.32; H, 2.44; N, 3.48.

Method Two

A. (2S)-4,4,4-Trifluoro-2-{[(1R)-1-phenylethyl]amino}-3-(trifluoromethyl)butan-1-ol hydrochloride salt To a 4 L plastic beaker 50.0 g (127.0 mmol, 1.0 equiv) of 4,4,4,4',4',4'-hexafluoro-N-[(1R)-1-phenylethyl]-L-valine phenylmethyl ester hydrochloride (prepared analogously to the method described in Helvetica Chimica Acta (1998), 81(1), 182-186) and 800 mL of anhydrous toluene were added. The solid only partially dissolved. Then, 129 mL of 1.0 N NaOH was added in portions so that the pH=7. The contents of the beaker were transferred to a 2 L separatory funnel and the aqueous (bottom) layer was removed. The remaining (top) layer was washed with 1×350 mL of water and extracted. The toluene layer was then dried with 52.5 g of solid $Na_2SO_4$ for 30 min. The solution was then filtered and transferred to a 3 L, 3-neck round bottom flask that was capped so that the solution remained anhydrous.

After 24 h, the reaction flask was equipped with a magnetic stirrer, addition funnel, and Argon inlet. The solution was cooled with a dry ice/acetone bath for 35 min. Then, 380 mL of 1.0 M (2.99 equiv) DIBAL-toluene was quickly added over a period of 20 min. The internal temperature never rose above −46° C. and the bath remained constant at −79° C. The reaction was stirred at this low temperature for an additional 40 min, the bath was removed, and the reaction was stirred at 25° C. for 4.5 h.

The reaction was checked for completion by HPLC. The reaction was cooled with an ice/water bath and then quenched by adding 26 mL of a freshly prepared solution of 10% NaOH in portions so that the temperature never rose above 45° C. After 15 min of stirring, the ice bath was removed and 106.3 g of NaCl and 79.5 g of $Na_2SO_4$ was added to the reaction flask. The solution was stirred at 25° C. for 1 hour with a mechanical stirrer.

The reaction was then filtered and the remaining solids were washed well with toluene. The filtrates were concentrated in vacuo and 39.8 g (99%) of the free base of the title compound was isolated as a yellow oil.

The HCl salt was prepared by dissolving the 39.8 g of the yellow oil in 520 mL of $Et_2O$ in the 2 L round bottom flask. The solution was cooled with an ice/water bath for 30 min. Then 120 mL of 1 N HCl in $Et_2O$ (purchased from Aldrich) was added to the solution. After stirring at 0° C. for 20 min, the solution solidified and ceased stirring and the solution was warmed to 25° C. and stirred for 20 min. The solution was filtered and washed with 200-300 mL of cold $Et_2O$, and dried under vacuum overnight to give 37.036 g (83%) of the title compound as a powdery white solid. Mass Spectrum (+ESI): 316.1 $[M+H]^+$.

B. (2S)-2-Amino-4,4,4-trifluoro-3-(trifluoromethyl)butan-1-ol hydrochloride salt A 2 L Parr bottle was flushed with N₂ and 9.374 g (0.10 g/mmol) of 10% Pd/C was carefully added to the flask. Then, 50 mL of anhydrous MeOH was added and the flask was carefully swirled. A solution of 36.136 g (98.3 mmol, 1.0 equiv) of (2S)-4,4,4-trifluoro-2-{[(1R)-1-phenylethyl]amino}-3-(trifluoromethyl)butan-1-ol hydrochloride salt dissolved in 50 mL of MeOH was added to the flask. The Parr bottle was flushed with more N₂, and then capped. The heterogeneous reaction mixture was hydrogenated at 45 psi for 2 h. The reaction was checked for completion by ¹H NMR. The reaction was worked up by filtering through a 1-inch pad of the Celite® reagent and washing with 1.5-2 L of MeOH. The filtrates were combined and concentrated in vacuo to give 28.56 g (100%) of (2S)-2-amino-4,4,4-trifluoro-3-(trifluoromethyl)butan-1-ol hydrochloride salt as a cream-colored solid. Further purification by triturating with 80 mL of 1:1 hexane:Et₂O can also be performed. Mass Spectrum (+ESI): 212.1 [M+H]⁺.

C. 4-Chloro-N-[(1S)-3,3,3-trifluoro-1-(hydroxymethyl)-2-(trifluoromethyl)propyl]benzenesulfonamide To a 1-L round bottom flask containing (2S)-2-amino-4,4,4-trifluoro-3-(trifluoromethyl)butan-1-ol hydrochloride salt (33.96 g, 128.8 mmol) was added 500 mL of anhydrous CH₂Cl₂. The solution was stirred at 25° C. for 15 min and then BSA (38 mL, 155.4 mmol, 1.21 equiv) was added to the flask. The addition of this reagent aided in dissolution of the solid. Triethylamine (52 mL, 373.1 mmol, 2.9 equiv) was then added to the reaction, the reaction warmed slightly, and a white gas formed and became progressively darker orange as the reaction progressed. Then, DMAP (4.45 g, 36.43) was added and the reaction was stirred an additional 20 min.

To the reaction was then added a solution of 4-chlorobenzenesulfonyl chloride (36.225 g, 171.6 mmol, 1.33 equiv) that had been dissolved in 66 mL of anhydrous CH₂Cl₂. Addition of this reagent caused the color of the reaction to change from dark-brown to light yellow. The reaction was stirred at 25° C. overnight. The reaction was checked for completion by HPLC as well as ¹H NMR. The reaction was quenched by adding 153 mL of tetrahydrofuran (THF) and 271 mL of 5% HCl (freshly prepared). The resulting solution was transferred to a 1 L separatory funnel and the aqueous layer was drained off. The resulting organic layer was washed with the following: 1×250 mL 5% NaHCO₃, 1×250 mL of H₂O, and 1×200 mL sat'd NaCl. The organic layer was dried over Na₂SO₄, filtered, and evaporated to give 52.5 g (100%) of the impure title compound as a red-oil. A filter chromatography (2 inches silica gel, 2 L filter funnel, 1 L size fractions, loaded onto the column with 30% EtOAc/hexanes, eluted with a gradient of 30% EtOAc/hexanes to 100% EtOAc) gave 46.3 g of mixed fractions, and 8.0 g of pure material. The material isolated was recombined (66.9 g) and chromatographed (2 inches silica gel, 2 L filter funnel, 1 L size fractions, loaded onto the column absorbed onto 120 g SiO₂, and eluted with a gradient of 10% EtOAc/hexanes to 50% EtOAc/hexanes) giving 37.2 g of pure title compound as a cream-colored solid. This material was triturated with 83 mL of a 10% EtOAc:hexanes solution and the resulting solid was collected by filtration and dried under vacuum overnight, yielding 32.084 g (65%). Mass Spectrum (−ESI): 383.9 [M−H]⁻.

Anal. Calc'd for C₁₁H₁₀ClF₆NO₃S: C, 34.25; H, 2.61; N, 3.63; Found: C, 34.32; H, 2.44; N, 3.48.

Example 2

4-Chloro-N-[(1S)-4,4,4-trifluoro-1-hydroxymethyl-2-(2,2,2-trifluoro-ethyl)-butyl]-benzenesulfonamide

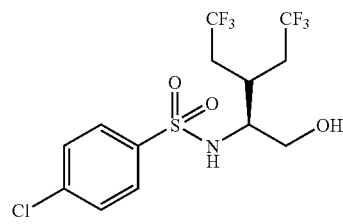

Method One

A. (3,3,3-Trifluoropropyl)-triphenylphosphonium iodide

To a solution of 1-iodo-3,3,3-trifluoropropane (19.3 g, 86.1 mmol) in toluene (50 mL) at 23° C. was added triphenylphosphine (25.8 g, 98.5 mmol). The reaction mixture was warmed to reflux and stirred for 28 h. The resulting mixture was cooled to 0° C. in an ice bath and filtered to collect the white solid product. The product was washed with toluene (3×) and air-dried to afford the pure product as white solid (33.4 g, 80%).

B. 4,4,4-Trifluoro-2-(triphenyl-λ⁵-phosphanylidene)-butyric acid ethyl ester To a suspension of (3,3,3-trifluoropropyl)-triphenylphosphonium iodide (105 g, 20.6 mmol) in THF (40 mL) at −78° C. was added slowly a solution of lithium bis(trimethylsilyl)amide (1.0 M in THF, 41.2 mL) through an addition funnel under nitrogen. The resulting mixture was stirred at −78° C. for 15 min followed by dropwise addition of a solution of ethylchloroformate (3.92 mL, 41.2 mmol) in THF (40 mL). The reaction mixture was then allowed to warm up to 25° C. while stirring. The reaction mixture was partitioned between EtOAc (300 mL) and brine (300 mL). The organic layer was dried over Na₂SO₄ and evaporated in vacuo to afford a crude solid which was purified by flash chromatography (EtOAc: hexanes 1:1) to provide a light tan solid (7.18 g) in 81% yield. Mass Spectrum (+ESI): 431 [M+H]⁺.

C. 4,4,4-Trifluoro-2-(2,2,2-trifluoroethyl)-but-2-enoic acid ethyl ester

To a solution of 4,4,4-trifluoro-2-(triphenyl-λ⁵-phosphanylidene)-butyric acid ethyl ester (2.0 g, 4.65 mmol) in THF (5 mL) was added 1 mL of trifluoroacetaldehyde hydrate (tech.). The mixture was sealed in a pressure tube and heated at 100° C. for 3.5 h. After cooling to 23° C., the reaction mixture was eluted through a pad of silica gel (100 g) and Na₂SO₄ with Et₂O (100 mL) to remove the by-products triphenylphosphine oxide and water. The eluent was distilled to remove Et$_2$O and to afford the product as a colorless liquid (1.0 g, 86%).

D. 4,4,4-Trifluoro-2-(2,2,2-trifluoroethyl)-butyric acid ethyl ester 4,4,4-Trifluoro-2-(2,2,2-trifluoroethyl)-but-2-enoic acid ethyl ester (5.0 g, 20.0 mmol) in THF (20 mL) was treated with Pd/C (2.5 g, 5%), and H$_2$ (1 atm.) at 25° C. for 17 h. The reaction mixture was filtered through a pad of the Celite® reagent, rinsed with Et$_2$O (50 mL) and the filtrate was distilled to remove Et$_2$O and THF to afford the product as colorless liquid (5.0 g, 99%).

E. 4,4,4-Trifluoro-2-(2,2,2-trifluoroethyl)-butan-1-ol

To a suspension of LAH (1.0 g) in Et$_2$O (100 mL) at 25° C. was added slowly 4,4,4-trifluoro-2-(2,2,2-trifluoroethyl)-butyric acid ethyl ester (5.0 g, 19.8 mmol). The resulting mixture was stirred at reflux for 4 h. The cooled reaction mixture was quenched by sequential addition of water (1.0 mL), 15% NaOH in water (1.0 mL) and water (3.0 mL). After the resulting mixture was allowed to stir at 25° C. for 17 h, Na$_2$SO$_4$ (20 g) was added and stirring at 25° C. continued for 1 h. The resulting suspension was filtered through a pad of the Celite® reagent and Na$_2$SO$_4$. The filtrate was distilled to remove all solvents to afford the desired product as a colorless liquid (1.7 g, 41%). Mass Spectrum (−ESI): 269 [M+OAc]$^-$.

F. 4,4,4-Trifluoro-2-(2,2,2-trifluoroethyl)-butyraldehyde

To a solution of 4,4,4-trifluoro-2-(2,2,2-trifluoroethyl)butan-1-ol (5.0 g, 24 mmol) in CH$_2$Cl$_2$ (80 mL) was added Dess-Martin periodinane reagent (10 g, 24 mmol). The reaction mixture was subsequently stirred for 20 hours at 25° C. The solution was diluted with Et$_2$O (200 mL) and a 1:1 mixture of 10% sodium thiosulfate and saturated NaHCO$_3$ (200 mL) was added. The mixture was stirred rapidly for 10 min until both phases were clear. The layers were separated and the aqueous phase was extracted with Et$_2$O (100 mL). The combined organic layers were washed with brine (100 mL), dried over Na$_2$SO$_4$, filtered and concentrated to 50% of its original volume to give 4,4,4-trifluoro-2-(2,2,2-trifluoroethyl)-butyraldehyde that was used as is for the subsequent reaction.

G. 4-Methyl-N-[(1S)-4,4,4-trifluoro-2-(2,2,2-trifluoroethyl)butylidene]benzenesulfinamide To the crude organic extract of 4,4,4-trifluoro-2-(2,2,2-trifluoroethyl)butyraldehyde in CH$_2$Cl$_2$ (80 mL) was added titanium (IV) ethoxide (22 g, 96 mmol) followed by (S)-(+)-toluene sulfinimide (4.64 g, 28.8 mmol) and the solution was heated to reflux for 15 h. The mixture was then cooled and water (30 mL) was added. The suspension was filtered through a pad of the Celite® reagent and the filter cake was washed with CH$_2$Cl$_2$. The layers of the filtrate were separated. The combined organic extracts were washed with brine, dried over Na$_2$SO$_4$, filtered, and concentrated. The crude product was purified by Biotage Flash™ 40 chromatography, eluent: 20:80 EtOAc-hexanes, to afford the title compound as a yellow oil (1.12 g) in 13% yield. Mass Spectrum (−ESI): 344 [M−H]$^-$.

H. 4-Methyl-benzenensulfinic acid [1S-1-cyano-4,4,4,-trifluoro-2-(2,2,2-trifluoroethyl)-butyl]amide To diethylaluminum cyanide (1M in toluene, 3.9 mL, 3.9 mmol) in THF (6 mL) at 0° C. was added isopropyl alcohol (300 µL, 3.9 mmol). After 15 min, this solution was added to a −78° C. solution of 4-methyl-N-[(1S)-4,4,4-trifluoro-2-(2,2,2-trifluoroethyl)butylidene]benzenesulfinamide (0.903 g, 2.6 mmol) in THF (25 mL). The solution was kept at −78° C. for 15 min and then allowed to warm slowly to 25° C. Saturated aqueous NH$_4$Cl (30 mL) was added and reaction mixture was extracted with EtOAc (3×50 mL). The combined organic layers were washed with brine, dried over Na$_2$SO$_4$ and evaporated to a crude oil which was purified by flash chromatography, eluent: 20:80 EtOAc:hexanes, to provide a clear oil (640 mg) in 66% yield. Mass Spectrum (−ESI): 371 [M−H]$^-$.

I. (2S)-2-Amino-5,5,5-trifluoro-3-(2,2,2-trifluoroethyl)-pentanoic acid methyl ester A solution of 4-methyl-benzenensulfinic acid [1S-1-cyano-4,4,4,-trifluoro-2-(2,2,2-trifluoroethyl)-butyl]amide (0.20 g, 0.53 mmol) in concentrated HCl (5 mL) was heated to 100° C. for 19 h. The solvent was removed in vacuo and azeotroped with toluene (2×5 mL). The crude solid was taken up in anhydrous methanol (5 mL), acetyl chloride (0.50 mL) was carefully added, and the reaction was heated to reflux for 18 h. The solvent was removed in vacuo to afford a crude product which was partitioned between EtOAc and 2M HCl. The aqueous layer was extracted with EtOAc. The aqueous layer was then treated with sat. NaHCO$_3$ until pH>10 and extracted with EtOAc (3×10 mL). The organic layer was dried over Na$_2$SO$_4$ and evaporated leaving an oil (90.9 mg) in 64% yield. Mass Spectrum (+ESI): 268 [M+H]$^+$.

J. (2S)-2-(4-Chloro-benzenesulfonylamino)-5,5,5-trifluoro-3-(2,2,2-trifluoroethyl)-pentanoic acid methyl ester 4-Chlorophenyl sulphonyl chloride (211 mg, 1.00 mmol) was added to a solution of (2S)-2-amino-5,5,5-trifluoro-3-(2,2,2-trifluoroethyl)-pentanoic acid methyl ester (267 mg, 1.00 mmol) and pyridine (0.45 mL, 3.00 mmol) in CH$_2$Cl$_2$ (5 mL) and the reaction was subsequently stirred for 18 h at 25° C. The solvent was removed in vacuo and the residue was dissolved in EtOAc (20 mL). This solution was washed with 1M HCl (2×10 mL) and brine (10 mL), dried over Na$_2$SO$_4$ and evaporated to afford a crude oil which was purified by flash chromatography eluting with 20:80 EtOAc:hexanes to provide the title compound (380 mg) as an oil in 86% yield. Mass Spectrum (−ESI): 446.0 [M−H]$^-$.

K. 4-Chloro-N-[(1S)-4,4,4-trifluoro-1-hydroxymethyl-2-(2,2,2-trifluoroethyl)-butyl]-benzenesulfonamide A solution of (2S)-2-(4-chloro-benzenesulfonylamino)-5,5,5-trifluoro-3-(2,2,2-trifluoroethyl)-pentanoic acid methyl ester (130 mg, 0.30 mmol) in THF (5 mL) was treated with LiBH$_4$ (2M THF, 0.3 mL, 0.58 mmol) for 18 hours at 25° C. The reaction was carefully quenched by the addition of 2M HCl and the organic solvent removed in vacuo. The aqueous layer was extracted with EtOAc (2×10 mL). The organic layers were combined, dried over Na$_2$SO$_4$ and evaporated to afford a crude oil which was purified by flash chromatography eluting with 30:70 EtOAc:hexanes to provide the title compound as a white solid (220 mg) in 63% yield. Mass Spectrum (−ESI): 412.0 [M−H]⁻.

Method Two

A. (3,3,3-Trifluoropropyl)-triphenylphosphonium iodide

A solution of 1,1,1-trifluoro-3-iodopropane (263.1 g, 1.17 mol) and triphenylphosphine (924.4 g, 3.52 mol) in toluene (950 mL) was stirred at reflux for 12 h. The solid product precipitated from the reaction mixture throughout the course of the reaction. The reaction was allowed to cool to ambient temperature and then cooled to ~5° C. in an ice bath. The solid precipitate was isolated by filtration and dried in vacuo at 25° C. to give a white powder (526.5 g, 92%).

Anal. Calc'd for $C_{21}H_{19}F_3IP$: C, 51.87; H, 3.94. Found: C, 51.99; H, 3.90.

B. 4,4,4-Trifluoro-2-(triphenyl-$\lambda^5$-phosphanylidene)-butyric acid ethyl ester A suspension of (3,3,3-trifluoropropyl)triphenylphosphonium iodide (194.5 g, 0.4 mol) in THF (anhydrous, 800 mL) was cooled to −5° C. in an ice/brine bath under nitrogen. To this suspension, lithium bis(trimethylsilyl)amide (1.0 M in THF, 800 mL, 0.8 mol) was added drop-wise over 2 h. The temperature was maintained below 5° C. throughout the addition. The reaction mixture was then cooled to −75° C. in a dry ice/acetone bath. To this solution, ethylchloroformate (76.5 mL, 0.8 mol) was added drop-wise over 30 min. The reaction was stirred at −75° C. for an additional hour and allowed to warm to 25° C. overnight. The reaction mixture was poured onto brine (1.5 L) and stirred for 30 min. The layers were separated and the organic layer was washed with brine (200 mL). The aqueous layer was washed with $CH_2Cl_2$ (2×200 mL) and the combined organics were concentrated to a residue. This residue was redissolved in $CH_2Cl_2$ (500 mL), dried over $MgSO_4$, and filtered through a plug of magnasol. The solvent was reduced to a minimum (~100 mL) in vacuo and the product was precipitated with hexanes (250 mL). The solvent was completely removed in vacuo and the solid product was triturated with hexanes (500 mL). The solid was isolated by filtration and dried overnight in vacuo at 25° C. to give a beige powder (152.8 g, 89%).

Anal. Calc'd for $C_{24}H_{22}F_3O_2P$: C, 66.97; H, 5.15. Found: C, 66.37; H, 5.28.

C. 4,4,4-Trifluoro-2-(2,2,2-trifluoroethyl)-but-2-enoic acid ethyl ester

Trifluoroacetaldehyde hydrate (150 g, technical grade, pH 1) was treated with stirring with solid, anhydrous sodium bicarbonate (15 g, powder) to result in a mildly foaming suspension. Anhydrous magnesium sulfate powder (60 g) was added, followed by addition of MTBE (300 mL) to result in a mildly exothermic reaction. The suspension was kept in a water bath at 10° C. for 10 min and filtered through a fluted filter funnel and washed with MTBE (2×250 mL). The filtrate (pH 7.2) was charged into a 2 L "Parr" pressure reactor containing the starting ylide, prepared as described in Example 2, Method 2, step B, (204 g, 0.474 mol). To the mixture was added anhydrous magnesium sulfate powder (60 g). The reaction vessel was heated to 70-75° C. with stirring for 15 h. The pressure in the "Parr" reactor rose to 18-21 psi. The reaction was cooled to ambient temperature and the mixture was filtered. The filter cake was washed with MTBE. The filtrate was distilled at 60-70 mm/Hg to remove most of the MTBE in the first fraction and collected the remainder in the second fraction. The pressure for the second fraction was reduced to 20 mm/Hg to yield 121.7g. The second fraction (121.7 g) was redistilled at 20 mm/Hg with a bath temperature at 80° C. to yield a main fraction of a low viscosity liquid, (103.5 g, 87%) b.p. 53-55° C. Mass Spectrum (+ESI): 251 [M+H]⁺

D. 4,4,4-Trifluoro-2-(2,2,2-trifluoroethyl)-butyric acid ethyl ester 4,4,4-Trifluoro-2-(2,2,2-trifluoroethyl)but-2-enoic acid ethyl ester (225 g, 0.9 mol) was dissolved in THF (700 mL) and treated with 5% Pd/C (17 g). The mixture was reduced by hydrogenation in a "Parr" shaker in a 2.5 L pressure bottle at 50 psi. The reaction was exothermic to 45° C. and was controlled by interrupting the shaking motion of the "Parr" shaker. The reaction was completed in approximately 2 h. The reaction mixture was filtered through a 2-inch bed of the Solka Floc® reagent/magnesium sulfate to give a clear, colorless solution of the title compound (225 g in 1182 g of tetrahydrofuran, quantitative yield). Mass Spectrum (+ESI): 253 [M+H]⁺

E. 4,4,4-Trifluoro-N-methoxy-N-methyl-2-(2,2,2-trifluoroethyl)butyramide

N,O-Dimethylhydroxylamine hydrochloride (90 g, 092 mol) was added to a solution of 4,4,4-trifluoro-2-(2,2,2-trifluoroethyl)butyric acid ethyl ester (116.28 g, 0.46 mol) in THF (610.8 g weight of the solution). The mixture was cooled to −15 to −20° C. with a dry ice/acetone bath. To the reaction mixture was added dropwise a solution of isopropyl magnesium chloride (924 mL, 2M in THF, 1.848 mol) over a period of 1 h, keeping the temperature at −15 to −20° C. After the addition, the reaction was stirred at that temperature for 30 min.

The reaction was quenched by adding dropwise HCl (2N, 600 mL 1.2 mol). The reaction proceeded at a very exothermic rate for the first 50 mL. The temperature did not exceed 3° C. Initially, a thick suspension formed which subsequently became a clear solution with two layers.

The mixture was extracted with MTBE (1.5 L). The aqueous phase was re-extracted with MTBE (0.5 L). The combined organic extracts were washed with brine (2×0.5 L). The organic phase was dried over anhydrous magnesium sulfate powder, filtered and the filtrate was concentrated in vacuo at max. 35° C. to an oil of weight of 121 g. The oil was distilled at 15 mm/Hg/b.p. 64-68° C. to give the title compound as oil. Mass Spectrum (+ESI): 268 [M+H]⁺

F. 4,4,4-Trifluoro-2-(2,2,2-trifluoro-ethyl)-butyraldehyde

To a solution of 4,4,4-trifluoro-N-methoxy-N-methyl-2-(2,2,2-trifluoroethyl)-butyramide (2.67 g, 10 mmol) in $CH_2Cl_2$ (10 mL), diisobutylaluminum hydride (2.9 mL, 16 mmol) was added over 10 min at −70° C. The reaction mixture was stirred at −70° C. for 40 min, then transferred via a cannula to a flask containing 30 mL of 2N HCl at 0° C. 10 mL of conc. HCl was added and the mixture was stirred at 25° C. for 30 min. Phases were split and the aqueous phase was extracted with 5 mL of $CH_2Cl_2$. The combined organic phase was washed with brine and dried over $MgSO_4$. NMR analysis of the solution using an internal standard indicated formation of the title product in 65% yield. The solution was used as such for further transformations.

G. 4-Methyl-N-[(1S)-4,4,4-trifluoro-2-(2,2,2-trifluoroethyl)butylidene]benzenesulfinamide To a $CH_2Cl_2$ solution of 4,4,4-trifluoro-2-(2,2,2-trifluoroethyl)butyraldehyde (92 mL; contained 8.8 mmol of the aldehyde; prepared as described above) titanium isopropoxide (13.4 mL, 44 mmol, 97% pure) and (S)-(+)-p-toluenesulfinamide were added. The reaction mixture was stirred at 40° C. for 5 h, cooled to 25° C., and poured into a mixture of $CH_2Cl_2$ (100 mL) and water (50 mL) at 0° C. The mixture was stirred at 25° C. for 1 h, then filtered through the Celite® reagent. The phases were separated and the aqueous phase was extracted with $CH_2Cl_2$. The combined organic fraction was washed with brine, dried over $MgSO_4$, and concentrated. The resultant crude mixture was dissolved in 3:7 EtOAc-heptane, passed through a pad of silica gel, and concentrated to afford 2.11 g (69%) of the title product. Mass Spectrum (+ESI): 346 $[M+H]^+$.

H. 4-Methyl-benzenensulfinic acid [1S-1-cyano-4,4,-trifluoro-2-(2,2,2-trifluoroethyl)-butyl]amide THF (6 mL) and diethylaluminum cyanide (3 mL of 1M toluene solution, 3 mmol) were placed in a 50-mL flask. Isopropanol (0.153 mL, 2 mmol) was added at 0° C. The mixture was stirred at 0° C. for 15 min, then transferred via a cannula to a flask containing THF (18 mL) and 4-methyl-N-[(1S)-4,4,4-trifluoro-2-(2,2,2-trifluoroethyl)butylidene]benzenesulfinamide (0.69 g, 2 mmol) at −70° C. The reaction mixture was warmed up to 25° C. and stirred for 1 h. The mixture was quenched by the addition of 50 mL of $NH_4Cl$ solution at 0° C. The resultant suspension was filtered through the Celite® reagent. The Celite® pad was washed with EtOAc. The phases were separated. The aqueous phase was extracted with EtOAc. The combined organic fraction was washed with brine, dried, and concentrated to afford 0.72 g of the title product as a 10:1 mixture of diastereomers. Mass Spectrum (+ESI): 373 $[M+H]^+$.

I. (2S)-2-Amino-5,5,5-trifluoro-3-(2,2,2-trifluoroethyl)-pentanoic acid methyl ester A solution of 4-methyl-benzenensulfinic acid [(1S)-1-cyano-4,4,4,-trifluoro-2-(2,2,2-trifluoroethyl)-butyl]amide (10 g, 29 mmol) in concentrated HCl (200 mL) was heated under reflux for 15 h. The reaction was cooled to 25° C. A by-product, toluene-4-thiosulfonic acid S-p-tolyl ester, separated from the aqueous solution as a white crystalline solid and was filtered off. The aqueous filtrate was concentrated in vacuo to a sticky white solid. The crude amino acid was taken up in concentrated HCl (200 mL) and extracted with toluene (2×50 mL). The aqueous phase was concentrated in vacuo, co-evaporating with toluene (4×70 mL) to give a solid compound. The amino acid was dissolved in methanol (400 mL), treated with anhydrous HCl (4N, 100 mL) and refluxed for 72 h. The reaction was evaporated in vacuo to a foam (60% ester conversion by NMR). The reaction mixture was dissolved in methanol (300 mL) and treated with ethereal HCl (2N, 100 mL) and refluxed for 24 h. The solution was concentrated to a solid (80% ester conversion by NMR). The crude mixture was dissolved in water and extracted with MTBE. The aqueous phase was basified with solid $NaHCO_3$ and extracted with MTBE (2×100 mL). The organic layer was dried over $MgSO_4$, filtered and concentrated in vacuo to give the title compound as a solid. (4.6 g, 62%). Mass Spectrum (+ESI): 268 $[M+H]^+$.

J. (2S)-2-(4-Chloro-benzenesulfonylamino)-5,5,5-trifluoro-3-(2,2,2-trifluoro-ethyl)-pentanoic acid methyl ester To a solution of (2S)-2-amino-5,5,5-trifluoro-3-(2,2,2-trifluoroethyl)pentanoic acid methyl ester (2.173 g, 8.14 mmol) and pyridine (1.97 mL, 24.4 mmol) in $CH_2Cl_2$ (15 mL) was added a solution of 4-chlorobenzenesulfonyl chloride (2.66 g, 12.2 mmol, 97% pure) in $CH_2Cl_2$ (7 mL). The reaction mixture was stirred at 25° C. for 4 h, then cooled to 0° C. 15 mL of 1N HCl was added followed by 10 mL of dichloromethane. The phases were separated. The organic phase was washed with 1N HCl (15 mL) and brine, dried over $Na_2SO_4$, and concentrated to afford 4.1 g of crude mixture as a yellow solid. The solids were recrystallized from heptane (14 mL) to afford 3.035 g of the title product (84% yield). Mass Spectrum (+ESI): 442 $[M+H]^+$.

K. 4-Chloro-N-[(1S)-4,4,4-trifluoro-1-hydroxymethyl-2-(2,2,2-trifluoro-ethyl)-butyl]-benzenesulfonamide To a solution of (2S)-2-(4-chloro-benzenesulfonylamino)-5,5,5-trifluoro-3-(2,2,2-trifluoroethyl)pentanoic acid methyl ester (2.924 g, 6.6 mmol) in THF (30 mL) was added $LiBH_4$ (9.9 mL of 2M THF solution, 19.8 mmol) over 10 min at 4-6° C. The reaction mixture was stirred at 25° C. for 4 days. Additional $LiBH_4$ (6.6 mL of 2M THF solution, 13.2 mmol) was added and the reaction mixture was stirred at 25° C. for an additional 24 h. The reaction mixture was cooled to 0° C. and quenched by slow addition of 30 mL of 2N HCl (vigorous gas evolution). The mixture was partially concentrated in vacuum and extracted with EtOAc. The organic fraction was washed with brine, dried over $Na_2SO_4$, and concentrated to afford 2.66 g of crude product. The crude product was dissolved in a mixture of EtOAc (10 mL) and heptane (3 mL) at 55° C., cooled to 25° C., and the resultant suspension was aged for 48 h. Heptane (27 mL) was added, and the mixture was stirred at 25° C. for additional 48 h. The precipitate was filtered, and washed with heptane to afford 1.962 g of the title compound (72% yield), mp: 186-187° C. Chiral HPLC: 97% ee (Chiralcel® AD column 0.46×25 cm, 10% EtOH in hexanes) HRMS calc. (for M+H): 414.0360; found: 414.0359.

Anal. Calc'd for $C_{13}H_{14}ClF_6NO_3S$: C, 37.54; H, 3.52; N, 3.20; Found: C, 37.74; H, 3.41; N, 3.39.

Example 3

4-Chloro-3-methoxy-N-(3,3,3-trifluoro-1-hydroxymethyl-2-trifluoromethyl-propyl)-benzenesulfonamide

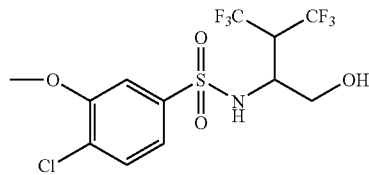

A. 4-Chloro-3-methoxy-benzene-lithium sulfinate

To a solution of 4-bromo-1-chloro-2-methoxy benzene (1.0 g, 4.5 mmol) in Et$_2$O (8 mL) at −70° C. was added n-BuLi (1.6 M in hexane, 3.4 mL, 5.4 mmol). After 2 h, a slow stream of SO$_2$ gas was bubbled into the reaction mixture for 7 min, then the mixture was stirred for 45 min. The cooling bath was removed and the reaction was then allowed to warm up to 25° C. After 15 min of additional stirring, the precipitate was filtered off, washed with Et$_2$O and air dried to give the product as an amorphous solid in quantitative yield. This solid was used without further purification in the next step.

B. 4-Chloro-3-methoxy-benzene sulfonyl chloride

To a two phase solution of CH$_2$Cl$_2$ and distilled water (6 mL each) was added 4-chloro-3-methoxy-benzene-lithium sulfinate (0.90 g, 4.23 mmol). The mixture was cooled to 0° C. and, while stirring vigorously, N-chlorosuccinamide (0.565 g, 4.23 mmol) was added portionwise over a 5 min period. The reaction was stirred for an addtional 1 hour then diluted with CH$_2$Cl$_2$ (25 mL). The organic phase was separated, washed with distilled water, dried over Na$_2$SO$_4$ and evaporated in vacuo to afford the product as a pale yellow oil (0.745 g, 73%).

C. 4-Chloro-3-methoxy-N-(3,3,3-trifluoro-1-hydroxymethyl-2-trifluoromethyl-propyl)-benzene-sulfonamide To a stirred solution of 4,4,4,4',4',4'-hexafluoro-dl-valinol (0.175 g, 0.83 mmol), triethylamine (0.13 mL, 0.91 mmol) and CH$_2$Cl$_2$ (4 mL) at 0° C., was added a previously dissolved mixture of 4-chloro-3-methoxy-benzene sulfonyl chloride (0.20 g, 0.83 mmol) in CH$_2$Cl$_2$ (1 mL). After 15 min, the ice bath was removed and the reaction allowed to reach 25° C. and stir 65 h. The reaction was then diluted with CH$_2$Cl$_2$ (20 mL) and poured into a separatory funnel containing a saturated NaHCO$_3$ solution. The organic phase was separated, washed sequentially with 1N HCl solution, distilled water, brine, dried over MgSO$_4$ and evaporated to afford the crude product which was purified by flash chromatography, eluent: 5:1 hexanes-ethyl acetate, to afford the product as a solid (55 mg, 16%). MS (−ESI) 414.0 ([M−H]$^-$).

Anal: Calc'd for C$_{12}$H$_{12}$ClF$_6$NO$_4$S.0.15 EtOAc C, 35.28; H, 3.10; N, 3.27. Found: C, 35.55; H, 2.80; N, 3.46.

Example 4

4-Chloro-N-(3,3,3-trifluoro-1-hydroxymethyl-2-trifluoromethyl-propyl)-3-trifluoromethyl-benzene-sulfonamide

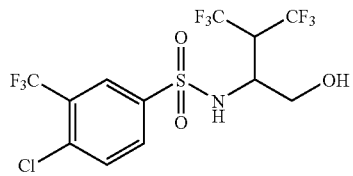

To a solution of 4,4,4,4',4',4'-hexafluoro-dl-valinol (0.10 g, 0.47 mmol) in CH$_2$Cl$_2$ (3 mL) was added a previously dissolved mixture of 4-chloro-3-trifluoromethyl-benzenesulfonyl chloride (0.132 g, 0.47 mmol) in CH$_2$Cl$_2$ (1 mL). Pyridine (77 μL, 0.95 mmol) was added and the mixture was stirred at 25° C. for 96 h. The reaction was diluted by adding CH$_2$Cl$_2$ (10 mL) and poured into a separatory funnel. It was then washed sequentially with 1 N HCl (2×), distilled water, brine, and dried over MgSO$_4$ and evaporated to afford the crude product which was purified by flash chromatography, eluent: 3:1 hexanes-ethyl acetate, to afford the product as a solid (35.5 mg, 17%). MS (−ESI) 452.0 ([M−H]$^-$).

Anal: Calc'd for C$_{12}$H$_9$ClF$_9$NO$_3$S.0.13 Hexane C, 33.02; H, 2.35; N, 3.01. Found: C, 33.03; H, 2.10; N, 2.94.

Example 5

4-Chloro-3-nitro-N-(3,3,3-trifluoro-1-hydroxymethyl-2-trifluoromethyl-propyl)-benzenesulfonamide

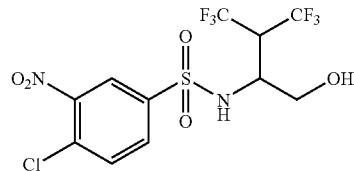

To a solution of 4,4,4,4',4',4'-hexafluoro-dl-valinol (0.50 g, 2.37 mmol), triethylamine (0.43 mL, 3.08 mmol) and CH$_2$Cl$_2$ (17.5 mL) at 0° C. was added a previously dissolved mixture of 4-chloro-3-nitro-benzenesulfonyl chloride (0.606 g, 2.37 mmol) in CH$_2$Cl$_2$ (5 mL). After 15 min, the ice bath was removed and the reaction allowed to warm up to 25° C. After 16 h, the reaction was then diluted with CH$_2$Cl$_2$ (20 mL) and poured into a separatory funnel containing a saturated NaHCO$_3$ solution. The organic phase was separated, washed sequentially with 1N HCl solution, distilled water, brine, dried over MgSO$_4$ and evaporated to afford the crude product which was purified using Biotage Flash™ chromatography, eluent: 3:1 hexanes-ethyl acetate, to afford the product as a solid (0.134 g, 13%). MS (−ESI) 428.9 ([M−H]$^-$).

Examples 6-17

3-Acetyl-N-(3,3,3-trifluoro-1-hydroxymethyl-2-trifluoromethyl-propyl)-benzenesulfonamide

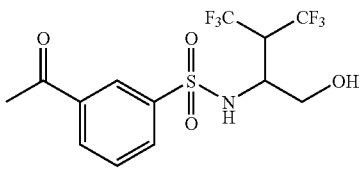

4,4,4,4',4',4'-Hexafluoro-dl-valinol (70 mg, 0.33 mmol) was added to a vial and dissolved in CH$_2$Cl$_2$ (1 mL). A previously dissolved mixture of 3-acetyl-benzenesulfonyl chloride (72.5 mg, 0.33 mmol) in CH$_2$Cl$_2$ (1 mL) was added, followed by pyridine (54 μL, 0.66 mmol). The vial was installed in an orbital shaker for 72 hours at 25° C. The product was isolated from the reaction mixture using Biotage Flash™ chromatography with hexanes-ethyl acetate, 3:1 as eluent to afford the product as a solid (23.7 mg, 18%).

The following compounds (Examples 6-17, Table 1) were prepared using 3-acetyl-benzenesulfonyl chloride, 4-difluoromethoxy-benzenesulfonyl chloride, 3-difluoromethoxy-benzenesulfonyl chloride, 4-ethyl-benzenesulfonyl chloride, 4-isopropyl-benzenesulfonyl chloride, 4-methoxy-benzenesulfonyl chloride, 3-methoxy-benzenesulfonyl chloride, 4-propyl-benzenesulfonyl chloride, 4-methyl-benzenesulfonyl chloride, 3-methyl-benzenesulfonyl chloride, 3-trifluoromethyl-benzenesulfonyl chloride, 4-trifluoromethyl-benzenesulfonyl chloride, and employing the procedure outlined in the previous example.

TABLE 1

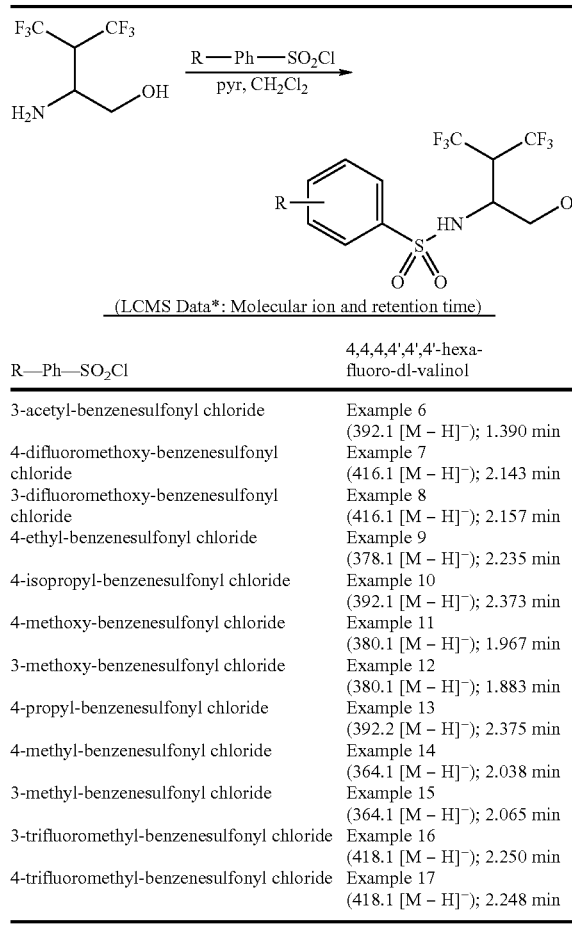

(LCMS Data*: Molecular ion and retention time)

| R—Ph—SO$_2$Cl | 4,4,4,4',4',4'-hexafluoro-dl-valinol |
|---|---|
| 3-acetyl-benzenesulfonyl chloride | Example 6 (392.1 [M − H]$^-$); 1.390 min |
| 4-difluoromethoxy-benzenesulfonyl chloride | Example 7 (416.1 [M − H]$^-$); 2.143 min |
| 3-difluoromethoxy-benzenesulfonyl chloride | Example 8 (416.1 [M − H]$^-$); 2.157 min |
| 4-ethyl-benzenesulfonyl chloride | Example 9 (378.1 [M − H]$^-$); 2.235 min |
| 4-isopropyl-benzenesulfonyl chloride | Example 10 (392.1 [M − H]$^-$); 2.373 min |
| 4-methoxy-benzenesulfonyl chloride | Example 11 (380.1 [M − H]$^-$); 1.967 min |
| 3-methoxy-benzenesulfonyl chloride | Example 12 (380.1 [M − H]$^-$); 1.883 min |
| 4-propyl-benzenesulfonyl chloride | Example 13 (392.2 [M − H]$^-$); 2.375 min |
| 4-methyl-benzenesulfonyl chloride | Example 14 (364.1 [M − H]$^-$); 2.038 min |
| 3-methyl-benzenesulfonyl chloride | Example 15 (364.1 [M − H]$^-$); 2.065 min |
| 3-trifluoromethyl-benzenesulfonyl chloride | Example 16 (418.1 [M − H]$^-$); 2.250 min |
| 4-trifluoromethyl-benzenesulfonyl chloride | Example 17 (418.1 [M − H]$^-$); 2.248 min |

*Hewlett Packard Series 1100 HPLC/MS, the Primesphere ™ C18 column, 0.2 × 3 cm column, elution gradient: 20% acetonitrile/water (0.1% HCOOH) to 100% acetonitrile (0.1% HCCOH) over 3 min at a flow rate of 0.6 mL/min.

Examples 18-21

4-Cyano-N-(3,3,3-trifluoro-1-hydroxymethyl-2-trifluoromethyl-propyl)-benzenesulfonamide

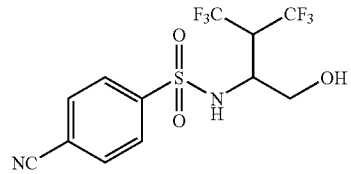

4,4,4,4',4',4'-Hexafluoro-dl-valinol (60 mg, 0.28 mmol) was added to a vial and dissolved in CH$_2$Cl$_2$ (1 mL). A previously dissolved mixture of 4-cyano-benzenesulfonyl chloride (56.5 mg, 0.28 mmol) in CH$_2$Cl$_2$ (1 mL) was added, followed by triethylamine (47.5 µL, 0.34 mmol). The vial was installed in an orbital shaker for 16 hours at 10° C. The product was isolated from the reaction mixture using Biotage Flash™ chromatography with hexanes-ethyl acetate, 5:1, as eluent to afford the product as a solid (13.7 mg, 13%).

The following compounds (Examples 18-21 Table 2) were prepared using 4-cyano-benzenesulfonyl chloride, 4-nitro-benzenesulfonyl chloride, 4-trifluoromethoxy-benzenesulfonyl chloride, 4-chloro-benzenesulfonyl chloride and employing the procedure outlined in the previous example.

TABLE 2

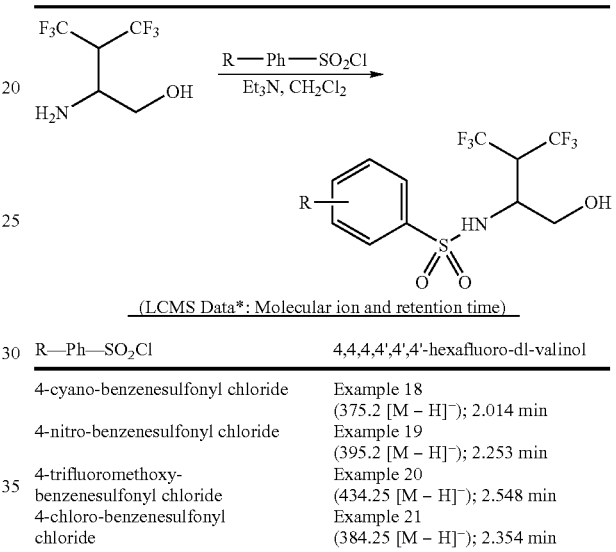

(LCMS Data*: Molecular ion and retention time)

| R—Ph—SO$_2$Cl | 4,4,4,4',4',4'-hexafluoro-dl-valinol |
|---|---|
| 4-cyano-benzenesulfonyl chloride | Example 18 (375.2 [M − H]$^-$); 2.014 min |
| 4-nitro-benzenesulfonyl chloride | Example 19 (395.2 [M − H]$^-$); 2.253 min |
| 4-trifluoromethoxy-benzenesulfonyl chloride | Example 20 (434.25 [M − H]$^-$); 2.548 min |
| 4-chloro-benzenesulfonyl chloride | Example 21 (384.25 [M − H]$^-$); 2.354 min |

*Hewlett Packard Series 1100 HPLC/MS, the Primesphere ™ C18 column, 0.2 × 3 cm column, elution gradient: 20% acetonitrile/water (0.1% HCOOH) to 100% acetonitrile (0.1% HCCOH) over 3 min at a flow rate of 0.6 mL/min.

Example 22

3,5-Difluoro-N-(3,3,3-trifluoro-1-hydroxymethyl-2-trifluoromethyl-propyl)-benzenesulfonamide

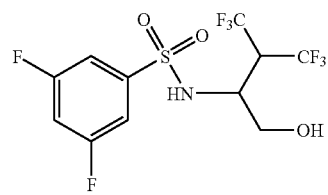

A. 2-(3,5-Difluoro-benzenesulfonylamino)-4,4,4-trifluoro-3-trifluoromethyl-butyric acid ethyl ester To a solution of 3,5-difluoro-benzenesulfonyl chloride (252 mg, 1.19 mmol) and 2-amino-4,4,4-trifluoro-3-trifluoromethyl-butyric acid ethyl ester (300 mg, 1.19 mmol) in CH$_2$Cl$_2$ (7 mL) was added anhydrous pyridine (144 µL, 1.77 mmol, 1.50 equiv.) and the vial capped and shaken for 72 h.

The reaction solution was transferred to a separatory funnel with $CH_2Cl_2$ (100 mL), washed with 1M citric acid solution (100 mL), water (50 mL×4), brine (100 mL), dried ($MgSO_4$), filtered and evaporated to give a white solid (300 mg, 59%). Mass Spectrum (−ESI): 427.8 [M−H]⁻

B. 3,5-Difluoro-N-(3,3,3-trifluoro-1-hydroxymethyl-2-trifluoromethyl-propyl)-benzenesulfonamide To a solution of 2-(3,5-difluoro-benzenesulfonylamino)-4,4,4-trifluoro-3-trifluoromethyl-butyric acid ethyl ester in anhydrous THF (5 mL) at 0° C. was added 2M $LiBH_4$ solution in THF (0.5 mL). The solution was allowed to warm to 25° C. and stir for 18 h. LC-MS of a reaction aliquot revealed unreacted starting material present. The reaction solution was immersed in an ice bath and 2M lithium borohydride (0.5 mL) was added and the solution allowed to warm to 25° C. and was stirred for 18 h. This procedure was repeated once more and, after 72 h, water was added to quench the reaction. The solvent was removed to give a tan solid which was transferred to a separatory funnel with EtOAc (100 mL) and washed with 1M citric acid solution (100 mL×2). The aqueous washings were combined and extracted with EtOAc (100 mL). The organic extracts were combined, washed with brine (100 mL), dried ($MgSO_4$), filtered and evaporated to give a peach colored solid (300 mg). This residue was adsorbed onto silica gel and purified by column chromatography, eluting with a solution of 50% EtOAc in hexanes to afford the alcohol (119 mg, 51%) as a white solid. Mass Spectrum (−ESI): 358.8 [M−H]⁻

Example 23

4-Chloro-3-methylsulfanyl-N-(3,3,3-trifluoro-1-hydroxymethyl-2-trifluoromethyl-propyl)-benzenesulfonamide

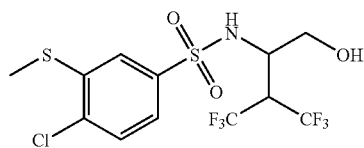

A. 4-Chloro-3-methylsulfanyl-benzenesulfonic acid

To a solution of 3-amino-4-chloro-benzenesulfonic acid (5.00 g, 24 mmol) in distilled water (38 mL) and concentrated HCl (6 mL, 72 mmol) at 0° C. was added sodium nitrite (1.99 g, 28.9 mmol) in $H_2O$ (10 mL). After 1.5 h, the mixture was allowed to warm to 25° C. and stirred for 1.5 h. Methyl disulfide (10.7 mL, 120 mmol) was added and the mixture heated to 70° C. for 18 h. The solvent was removed, in vacuo, to give an orange solid (16.7 g) that was used as is in the next reaction.

B. 4-Chloro-3-methylsulfanyl-benzenesulfonyl chloride

To a mixture of 4-chloro-3-methylsulfanyl-benzenesulfonic acid (24 mmol) in anhydrous toluene (100 mL) at 0° C. was added thionyl chloride (2.62 mL, 36 mmol). The ice bath was removed and the reaction heated to 85° C. for 5 h, then 70° C. for 18 h. Unreacted starting material was still present by LC-MS and thionyl chloride (5 mL) was added and the reaction stirred for 18 hours at 70° C. The solvent was removed to give a black oil (470 mg, 8%) that was used as is in the next reaction.

C. 2-(3,5-Difluoro-benzenesulfonylamino)-4,4,4-trifluoro-3-trifluoromethyl-butyric acid ethyl ester To a vial containing a solution of 2-amino-4,4,4-trifluoro-3-trifluoromethyl-butyric acid ethyl ester (179 mg, 0.708 mmol) and 4-chloro-3-methylsulfanyl-benzenesulfonyl chloride (182 mg, 0.708 mmol) in anhydrous $CH_2Cl_2$ (3 mL) was added pyridine (100 µL, 1.1 mmol). The vial was capped and shaken at 25° C. for 18 h. The solvent was removed, in vacuo, and the material adsorbed onto silica gel and purified by column chromatography eluting with $CH_2Cl_2$ to afford the ester (78 mg, 23%) as an amber colored oil.

D. 4-Chloro-3-methylsulfanyl-N-(3,3,3-trifluoro-1-hydroxymethyl-2-trifluoromethyl-propyl)-benzenesulfonamide To a solution of 2-(3,5-difluoro-benzenesulfonylamino)-4,4,4-trifluoro-3-trifluoromethyl-butyric acid ethyl ester (50 mg, 0.106 mmol) in anhydrous THF (5 mL) at 0° C. was added 2M $LiBH_4$ in THF (53 µL). The solution was allowed to warm to 25° C. After 18 h, the solution was quenched with 1N hydrochloric acid and the solvent removed in vacuo. The remaining aqueous phase was transferred to a separatory funnel with distilled water (100 mL) and extracted with EtOAc (100 mL). The organic layer was removed and the aqueous phase extracted with EtOAc (100 mL×2). The organic extracts were combined, washed with brine (100 mL), dried ($MgSO_4$), filtered and evaporated to give a clear oil which was purified by Gilson RP-HPLC (column YMC Combiprep 50×20 mm, gradient 10-100% $CH_3CN$: $H_2O$) to afford a white solid (11 mg, 24%). Mass Spectrum (−ESI): 431 [M−H]⁻.

Example 24

4-Chloro-3-fluoro-N-(3,3,3-trifluoro-1-hydroxymethyl-2-trifluoromethyl-propyl)-benzenesulfonamide

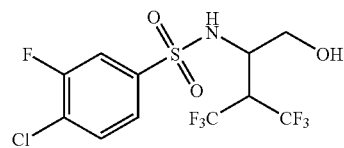

A. 4-Chloro-3-fluorobenzenesulfonyl chloride

The title compound was prepared using the method of Organic Syntheses Vol. 60, 121-124. A solution of 4-chloro-3-fluoro aniline (5 g, 0.034 mol) in glacial HOAc (10 mL) was added slowly to concentrated HCl (30 mL) to form a white precipitate. The mixture was cooled in a dry ice-ethanol bath. A solution of $NaNO_2$ (3.08 g, 0.045 mol) in $H_2O$ (5 mL) was added dropwise while stirring with a glass rod, maintaining the temperature at or below −5° C. The mixture was stirred intermittently while in the bath for 1 h. In a separate flask, HOAc (40 mL) was saturated with $SO_2$ using a gas dispersion tube (about 15 min). To this acetic acid solution was added cuprous chloride (0.68 g, 7 mmol), which gave a grey solution. The $SO_2$ was bubbled through until the solution turned green-blue. The solution was cooled in a dry ice-ethanol bath and the diazonium salt mixture was added in portions while stirring with a glass rod. After the addition was complete, the reaction was removed from the bath and allowed to come to 0° C. over 15 to 20 min. with occasional stirring. The reaction was poured onto ice (100 mL) and extracted with CH$_2$Cl$_2$ (2×100 mL). The combined organic layer was washed with saturated NaHCO$_3$ (3×40 mL), dried (Na$_2$SO$_4$), filtered and concentrated to afford a golden oil. The crude product was purified by silica gel column chromatography, eluting with a gradient of 10% to 15% CH$_2$Cl$_2$/hexanes to afford the title compound (5.5 g, 70%) as a golden oil. Mass Spectrum (−ESI): 209 [M−Cl+O]$^-$.

B. 2-(4-Chloro-3-fluoro-benzenesulfonylamino)-4,4,4-trifluoro-3-trifluoromethyl-butyric acid ethyl ester To a vial containing a solution of 4-chloro-3-fluorobenzenesulfonyl chloride (181 mg, 0.79 mmol) and 2-amino-4,4,4-trifluoro-3-trifluoromethyl-butyric acid ethyl ester (200 mg, 0.79 mmol) in anhydrous dichloroethane (3 mL) was added pyridine (192 µL). The vial was capped and shaken for 18 h. The solvent was removed in vacuo and the residue transferred to a separatory funnel with EtOAc (100 mL) and washed with distilled water (100 mL×2). The organic layer was removed and the combined aqueous washings were extracted with EtOAc (100 mL×2). The organic extracts were combined, washed with brine (100 mL), dried (MgSO$_4$), filtered, and evaporated to give a yellow solid (220 mg). This material was adsorbed onto silica gel and purified by column chromatography, eluent: HCCl$_3$, to afford a white solid (186 mg, 53%). Mass Spectrum (+ESI): 446 [M−H]$^+$.

C. 4-Chloro-3-fluoro-N-(3,3,3-trifluoro-1-hydroxymethyl-2-trifluoromethyl-propyl)-benzenesulfonamide 2-(4-Chloro-3-fluoro-benzenesulfonylamino)-4,4,4-trifluoro-3-trifluoromethyl-butyric acid ethyl ester (150 mg, 0.337 mmol) was dissolved in anhydrous THF (5 mL) and cooled to 0° C. 2M LiBH$_4$ in THF (168 µL in THF) was added and the solution allowed to warm to 25° C. After 18 h, LC-MS revealed unreacted starting ester present. Additional 2M LiBH$_4$ (200 µL) was added and the solution stirred for 24 h. The solution was cooled in an ice bath and 1N hydrochloric acid was added to quench the reaction. The solvent was removed in vacuo and the aqueous phase transferred to a separatory funnel with EtOAc (100 mL) and washed with distilled water (100 mL). The organic layer was removed and the aqueous phase extracted with EtOAc (100 mL×2). The organic extracts were combined, dried (MgSO$_4$), filtered and evaporated to give a white solid (111 mg). This material was purified by Gilson RP-HPLC (column YMC Combiprep 50×20 mm, gradient 10-100% CH$_3$CN: H$_2$O) to afford a white solid (63 mg, 46%). Mass Spectrum (+ESI): 401.8 [M−H]$^+$.

Example 25

4-Fluoro-3-methyl-N-(3,3,3-trifluoro-1-hydroxymethyl-2-trifluoromethyl-propyl)-benzenesulfonamide

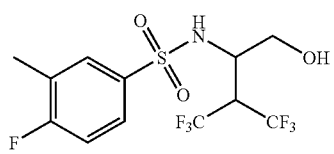

A. 4,4,4-Trifluoro-2-(4-fluoro-3-methyl-benzenesulfonylamino)-3-trifluoromethyl-butyric acid ethyl ester To a vial containing a solution of 4-fluoro-3-methylbenzenesulfonyl chloride (50 mg, 0.24 mmol) and 2-amino-4,4,4-trifluoro-3-trifluoromethyl-butyric acid ethyl ester (61 mg, 0.24 mmol) in anhydrous dichloroethane (1 mL) was added pyridine (58 µL, 0.719 mmol). The vial was capped and shaken for 18 h. The solvent was removed in vacuo and the residue transferred to a separatory funnel with EtOAc (100 mL) and washed with distilled water (100 mL×2). The organic layer was removed and the combined aqueous washings were extracted with EtOAc (100 mL×2). The organic extracts were combined, washed with brine (100 mL), dried (MgSO$_4$), filtered, and evaporated to give a white solid (66 mg). This material was purified by Gilson RP-HPLC (column YMC Combiprep 50×20 mm, gradient 10-100% CH$_3$CN: H$_2$O) to afford a white solid (29 mg, 28%). Mass Spectrum (−ESI): 424 [M−H]$^-$.

B. 4-Fluoro-3-methyl-N-(3,3,3-trifluoro-1-hydroxymethyl-2-trifluoromethyl-propyl)-benzenesulfonamide To a solution of 4,4,4-trifluoro-2-(4-fluoro-3-methyl-benzenesulfonylamino)-3-trifluoromethyl-butyric acid ethyl ester (29 mg, 0.068 mmol) in anhydrous THF (3 mL) at 0° C. was added 2M LiBH$_4$ (50 µL). The solution was allowed to warm to 25° C. After 18 h, the solution was quenched with 1N HCl and the solvent removed in vacuo. The remaining aqueous phase was transferred to a separatory funnel with distilled water (100 mL) and extracted with EtOAc (100 mL). The organic layer was removed and the aqueous phase extracted with EtOAc (100 mL×2). The organic extracts were combined, washed with brine (100 mL), dried (MgSO$_4$), filtered and evaporated to give a white solid (21 mg). This material was purified by Gilson RP-HPLC (column YMC Combiprep 50×20 mm, gradient 10-100% CH$_3$CN: H$_2$O) to afford a white solid (14 mg, 54%). Mass Spectrum (−ESI): 382 [M−H]$^-$.

Example 26

4-Fluoro-N-[3,3,3-trifluoro-1-(hydroxymethyl)-2-(trifluoromethyl)propyl]benzene sulfonamide

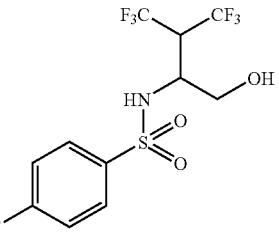

A. Methyl 4,4,4,4',4',4'-hexafluoro-dl-valinate

To a solution of 4,4,4,4',4',4'-hexafluoro-dl-valine (2.5 g, 11.11 mmol) in CH$_2$Cl$_2$-MeOH (4:1, 25 mL) at 0° C. was added TMS-diazomethane (2.0 M in hexane, 45 mmol, 23 mL) dropwise. The resulting neon greenish solution was stirred for 19 hours at 25° C. After this time period, the reaction was complete by TLC (10% MeOH in chloroform). After concentration, the resulting residue of methyl 4,4,4,4',4',4'-hexafluoro-dl-valinate (2.35 g) was used directly in the next step without further purification. Mass Spectrum (−ESI): 238 [M−H]$^-$.

B. 3,3,3-Trifluoro-2-(trifluoromethyl)-1-(hydroxymethyl)propylamine

A solution of LiBH$_4$ (2M THF, 19.66 mL, 39.33 mmol) was added to a solution of methyl 4,4,4,4',4',4'-hexafluoro-dl-valinate (2.35 g, 9.83 mmol) in THF (80 mL) at 0° C. The reaction was allowed to warm to 25° C. After 19 h, the reaction was cooled to 0° C. and 2M HCl was added to the reaction mixture very carefully until pH<2. The organic solvent was removed in vacuo and the aqueous layer was neutralized with sat NaHCO$_3$ until pH=7. The aqueous layer was extracted with EtOAc (2×50 mL) and the organic extracts were dried over Na$_2$SO$_4$ and concentrated to provide 3,3,3-trifluoro-2-(trifluoromethyl)-1-(hydroxymethyl)propyl amine as a yellow oil (1.7 g, 82% yield). The crude oil was of sufficient purity to utilize in the subsequent reaction. Mass Spectrum (−ESI): 210 [M−H]$^-$.

C. 4-Fluoro-N-[3,3,3-trifluoro-1-(hydroxymethyl)-2-(trifluoromethyl)propyl]benzene sulfonamide To a solution of 3,3,3-trifluoro-2-(trifluoromethyl)-1-(hydroxymethyl)propyl amine (79 mg, 0.374 mmol) in CH$_2$Cl$_2$ (1 mL) was added triethylamine (0.1 mL, 0.749 mmol) and 4-fluorobenzenesulfonyl chloride (80.5 mg, 0.4 mmol) in CH$_2$Cl$_2$ (1 mL). The solution was stirred for 20 hours at 25° C. and then concentrated. EtOAc (5 mL) was added and the solution was washed with 1M HCl (1 mL), brine (1 mL), dried over Na$_2$SO$_4$ and concentrated. The crude solid was purified by Biotage Flash™ chromatography, eluting with EtOAc/hexanes (1:4), to give 4-fluoro-N-[3,3,3-trifluoro-1-(hydroxymethyl)-2-(trifluoromethyl)propyl]benzene sulfonamide (2.5 mg) as a white solid.

The following compounds (Examples 26-40, Table 3) were prepared by using 4-fluorobenzenesulfonyl chloride, 3-fluorobenzenesulphonyl chloride, 2-fluorobenzenesulfonyl chloride, 3-chlorobenzenesulfonyl chloride, 2-chlorobenzenesulphonyl chloride, 4-bromobenzenesulfonyl chloride, 3-bromobenzenesulfonyl chloride, benzenesulfonyl chloride, 3,4-difluorobenzenesulfonyl chloride, 2,4-difluorobenzenesulphonyl chloride, 3,5-dichlorobenzenesulfonyl chloride, 2,3-dichlorobenzenesulfonyl chloride, 3,4-dichlorobenzenesulphonyl chloride, 3-chloro-4-fluorobenzenesulphonyl chloride, 2,3,4-trifluorobenzenesulfonyl chloride and employing the procedure outlined in Example 26.

TABLE 3

| RSO$_2$Cl | 3,3,3-trifluoro-2-(trifluoromethyl)-1-(hydroxymethyl)propylamine (MS Data*: Molecular ion) |
|---|---|
| 4-fluorobenzenesulfonyl chloride | Example 26 (370 [M + H]$^+$) |
| 3-fluorobenzenesulphonyl chloride | Example 27 (370 [M + H]$^+$) |
| 2-fluorobenzenesulfonyl chloride | Example 28 (370 [M + H]$^+$) |
| 3-chlorobenzenesulfonyl chloride | Example 29 (386 [M + H]$^+$) |
| 2-chlorobenzenesulphonyl chloride | Example 30 (386 [M + H]$^+$) |
| 4-bromobenzenesulfonyl chloride | Example 31 (431 [M + H]$^+$) |
| 3-bromobenzenesulfonyl chloride | Example 32 (431 [M + H]$^+$) |
| benzenesulfonyl chloride | Example 33 (351 [M + H]$^+$) |
| 3,4-difluorobenzenesulfonyl chloride | Example 34 (388 [M + H]$^+$) |
| 2,4-difluorobenzenesulphonyl chloride | Example 35 (388 [M + H]$^+$) |
| 3,5-difluorobenzenesulfonyl chloride | Example 36 (421 [M + H]$^+$) |
| 2,3-dichlorobenzenesulfonyl chloride | Example 37 (421 [M + H]$^+$) |
| 3,4-dichlorobenzenesulphonyl chloride | Example 38 (421 [M + H]$^+$) |
| 3-chloro-4-fluorobenzenesulphonyl chloride | Example 39 (404 [M + H]$^+$) |
| 2,3,4-trifluorobenzenesulfonyl chloride | Example 40 (455 [M + H]$^+$) |

Example 41

(S)-3,4-Dichloro-N-[3,3,3-trifluoro-1-(hydroxymethyl)-2-(trifluoromethyl)propyl]benzene sulfonamide

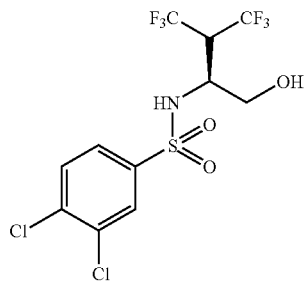

A. 2-(3,4-Dichloro-benzenesulfonylamino)-4,4,4-trifluoromethyl-butyric acid methyl ester To a solution of methyl 4,4,4,4',4',4'-hexafluorovalinate (prepared according to the method of Example 26, Part A, 1.1 g, 4.6 mmol) in CH$_2$Cl$_2$ (10 mL) at 25° C. was added pyridine (0.74 mL, 9.2 mmol) dropwise followed by 3,4-dichlorobenzenesulfonyl chloride (1.69 g, 6.90 mmol) in one portion. After 19 h, the reaction was complete by TLC (1:4 EtOAc-hexanes). After quenching with water (1.0 mL), the mixture was diluted with CH$_2$Cl$_2$ (30 mL). The organic layer was washed sequentially with 1N aqueous HCl (10 mL), saturated aqueous NaHCO$_3$ (10 mL) and brine (15 mL), dried over MgSO$_4$, filtered and concentrated to obtain a crude oil (2.1 g).

The crude product was purified by Biotage Flash™ chromatography, eluent: 1:6 EtOAc-hexanes, to afford 2-(3,4-dichloro-benzenesulfonylamino)-4,4,4-trifluoromethyl-butyric acid methyl ester as a white solid (1.62 g, 42%). Mass Spectrum (+ESI): 449 [M+H]$^+$.

B. 3,4-Dichloro-N-(3,3,-trifluoro-1-hydroxymethyl-2-trifluoromethyl-propyl)-benzene sulfonamide To a solution of 2-(3,4-dichlorobenzenesulfonylamino)-4,4,4-trifluoromethyl-butyric acid methyl ester (1.6 g, 3.57 mmol) in THF (20 mL) was added LiBH$_4$ in THF (5.82 mL, 11.64 mmol) under N$_2$ atmosphere at 0° C. The reaction was allowed to warm to 25° C. After 19 h, the reaction was cooled to 0° C., quenched with 2N HCl (slow addition), diluted with Et$_2$O (40 mL). The organic layer was washed sequentially with 1N aqueous HCl (10 mL), saturated aqueous NaHCO$_3$ (10 mL) and brine (15 mL), dried over MgSO$_4$, filtered and concentrated to obtain a crude oil (1.3 g). The crude product was purified by Biotage Flash™ chromatography, eluent: 1:6 EtOAc-hexanes, to afford 3,4-dichloro-N-(3,3,-trifluoro-1-hydroxymethyl-2-trifluoromethyl-propyl)-benzenesulfonamide as a white solid (1.13 g, 84%). The racemate was separated into its enantiomers via chiral separation using the following conditions: Instrument; Varian prep, column; Chiralcel® AS column (25×0.46 cm), mobile phase; 5% 2-butanol in CO$_2$ (200 bar) to obtain (S)-3,4-dichloro-N-(3,3,-trifluoro-1-hydroxymethyl-2-trifluoromethyl-propyl)-benzene sulfonamide as a white solid (0.320 g, 21% yield). Mass Spectrum (+ESI): 421 [M+H]$^+$.

S-isomer: HPLC Analytical purity =100% (Retention time=5.666 min) Chiral HPLC purity=95.02% (% ee=90.03)

Example 42

3,4,5-Trifluoro-N-(3,3,3-trifluoro-1-hydroxymethyl-2-trifluoromethyl-propyl)-benzene sulfonamide

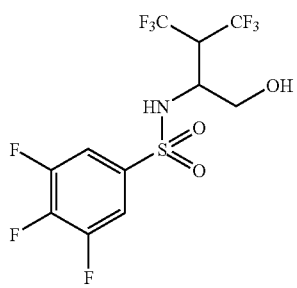

A. 4,4,4-Trifluoro-2-(3,4,5-trifluoro-benzenesulfonylamino)-3-trifluoromethyl-butyric acid ethyl ester A solution of 3,4,5-trifluorobenzenesulfonyl chloride (0.348 mL, 2.50 mmol) in CH$_2$Cl$_2$ (5 mL) was added to a solution of 2-amino-4,4,4-trifluoro-3-trifluoromethyl-butyric acid ethyl ester (0.4 g, 1.67 mmol) prepared as described (J. Med Chem. 1981, 24, 1043-1047), and pyridine (0.27 mL, 3.34 mmol) in CH$_2$Cl$_2$ (5 mL) at 0° C. and allowed to warm to 25° C. for 19 h. The solution was washed with 1M HCl (1 mL), brine (1 mL), dried over Na$_2$SO$_4$ and concentrated. The crude solid was purified by Biotage Flash™ chromatography, eluting with EtOAc/hexanes (1:4), to give 4,4,4-trifluoro-2-(3,4,5-trifluoro-benzenesulfonylamino)-3-trifluoromethyl-butyric acid ethyl ester (0.63 g, 85%) as a white solid. Mass Spectrum (+ESI): 448 [M+H]$^+$.

B. 3,4,5-Trifluoro-N-(3,3,3-trifluoro-1-hydroxymethyl-2-trifluoromethyl-propyl)-benzene sulfonamide To a solution of 4,4,4-trifluoro-2-(3,4,5-trifluoro-benzenesulfonylamino)-3-trifluoromethyl-butyric acid ethyl ester (0.54 g, 1.207 mmol) in THF (10 mL) was added LiBH$_4$ in THF (2.40 mL, 4.81 mmol) at 0° C. The reaction was allowed to warm to 25° C. for 19 h. The reaction was cooled to 0° C., quenched with 2N HCl (slow addition), and diluted with Et$_2$O (40 mL). The organic layer was washed sequentially with 1N aqueous HCl (10 mL), saturated aqueous NaHCO$_3$ (10 mL) and brine (15 mL), dried over MgSO$_4$, filtered and concentrated to obtain a crude oil (0.49 g). The crude product was purified by Biotage Flash™ chromatography, eluent: 1:7 EtOAc-hexanes, to afford 3,4,5-trifluoro-N-(3,3,3-trifluoro-1-hydroxymethyl-2-trifluoromethyl-propyl)-benzene sulfonamide as a white solid (0.150 g, 29.6%). Mass Spectrum (+ESI): 422 [M+H]$^+$.

Example 43

4-Chloro-N-[(1S,2S)-3,3,3-trifluoro-1-(hydroxymethyl)-2-methylpropyl]benzenesulfonamide

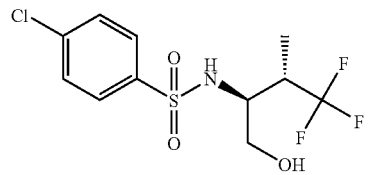

A. 2-Amino-4,4,4-trifluoro-3-methyl-butyric acid ethyl ester

Sodium azide (1.9 g, 28.7 mmol) and ethyl 2-bromo-3-methyl-4,4,4-trifluorobutyrate (5 g, 19.2 mmol) were placed in DMF (20 mL) and stirred for 48 h. The mixture was diluted with EtOAc (200 mL) and washed with brine (4×100 mL). The organic layer was dried over Na$_2$SO$_4$ and solvent removed. The crude oil was placed in EtOH (20 mL) with 5% Pd/C (1.6 g) and shaken for 6 hours under H$_2$ (50 psi). The reaction was filtered through the Celite® reagent and the solvent was removed providing a clear oil (1.9 g) in 50% yield.

B. (2S,3S)-2-(4-Chloro-benzenesulfonylamino)-4,4,4-trifluoro-3-methyl-butyric acid ethyl ester A solution of 4-chlorobenzene sulphonyl chloride (1.43 g, 6.75 mmol) in CH$_2$Cl$_2$ (20 mL) was added to a solution of 2-amino-4,4,4-trifluoro-3-methyl-butyric acid ethyl ester (0.9 g, 4.5 mmol) and pyridine (1.8 mL, 22.5 mmol) in CH$_2$Cl$_2$ (10 mL). The reaction was stirred at 25° C. for 18 h. Solvent was removed in vacuo and the crude oil was taken up in EtOAc (50 mL). The organic layer was washed with 1M HCl (2×15 mL) and brine (20 mL). The organic layer was dried over Na$_2$SO$_4$ and the solvent was removed. The diastereomers were separated by flash chromatography (20% EtOAc/hexanes) to provide diastereomer 1 (0.38 g) and diastereomer 2 (0.22 g). The 2S,3S isomer was then obtained from

C. 4-Chloro-N-[(1S,2S)-3,3,3-trifluoro-1-(hydroxymethyl)-2-methylpropyl]benzenesulfonamide A solution of lithium borohydride (2.0 M in THF, 0.23 mL) was added to a solution of (2S,3S)-2-(4-chloro-benzenesulfonylamino)-4,4,4-trifluoro-3-methyl-butyric acid ethyl ester (86 mg, 0.23 mmol) in THF (5 mL) and stirred for 12 h. Careful addition of 2N HCl (aq) was performed until pH<2. Organic solvent was removed in vacuo. The aqueous layer was extracted with EtOAc (2×20 mL) and organic layers were combined and washed with brine. The organic layer was dried over $Na_2SO_4$ and solvent removed in vacuo. The crude solid was purified by flash chromatography (20% EtOAc/hexanes) to provide a white solid (61 mg) in 80% yield. Mass Spectrum (–ESI): 330.0 [M–H]⁻.

Example 44

4-Chloro-N-[(1S,2R)-3,3,3-trifluoro-1-(hydroxymethyl)-2-methylpropyl]benzenesulfonamide

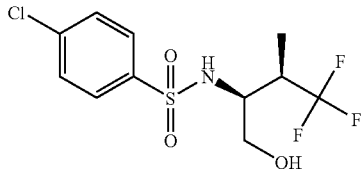

A. 2-Amino-4,4,4-trifluoro-3-methyl-butyric acid ethyl ester

Sodium azide (1.9 g, 28.7 mmol) and ethyl 2-bromo-3-methyl-4,4,4-trifluorobutyrate (5 g, 19.2 mmol) were placed in DMF (20 mL) and stirred for 48 h. The mixture was diluted with EtOAc (200 mL) and washed with brine (4×100 mL). The organic layer was dried over $Na_2SO_4$ and solvent was removed. The crude oil was placed in EtOH (20 mL) with 5% Pd/C (1.6 g) and shaken for 6 hours under $H_2$ (50 psi). The reaction was filtered through the Celite® reagent and solvent was removed providing a clear oil (1.9 g) in 50% yield.

B. (2S,3R)-2-(4-Chloro-benzenesulfonylamino)-4,4,4-trifluoro-3-methyl-butyric acid ethyl ester A solution of 4-chlorobenzene sulphonyl chloride (1.43 g, 6.75 mmol) in $CH_2Cl_2$ (20 mL) was added to a solution of 2-amino-4,4,4-trifluoro-3-methyl-butyric acid ethyl ester (0.9 g, 4.5 mmol) and pyridine (1.8 mL, 22.5 mmol) in $CH_2Cl_2$ (10 mL). The reaction was stirred at 25° C. for 18 h. Solvent was removed in vacuo and the crude oil was taken up in EtOAc (50 mL). The organic layer was washed with 1M HCl (2×15 mL) and brine (20 mL). The organic layer was dried over $Na_2SO_4$ and solvent was removed. The diastereomers were separated by flash chromatography (20% EtOAc/hexanes) to provide diastereomer 1 (0.38 g) and diastereomer 2 (0.22 g). The 2S,3R isomer was then obtained from diastereomer 1 by chiral HPLC (Chiralcel® AS column 2×25 cm, 13% IPA in hexanes, 21 mL/min, second peak RT=9.6 min) to provide a white solid (126 mg) in 7.6% yield.

C. 4-Chloro-N-[(1S,2R)-3,3,3-trifluoro-1-(hydroxymethyl)-2-methylpropyl]benzenesulfonamide A solution of lithium borohydride (2.0 M in THF, 0.34 mL) was added to a solution of (2S,3S)-2-(4-chloro-benzenesulfonylamino)-4,4,4-trifluoro-3-methyl-butyric acid ethyl ester (126 mg, 0.34 mmol) in THF (5 mL) and stirred for 12 h. Careful addition of 2N HCl (aq) was performed until pH<2. Organic solvent was removed in vacuo. The aqueous layer was extracted with EtOAc (2×20 mL) and organic layers were combined and washed with brine. The organic layer was dried over $Na_2SO_4$ and solvent removed in vacuo. The crude solid was purified by flash chromatography (20% EtOAc/hexanes) to provide a white solid (80 mg) in 71% yield. Mass Spectrum (–ESI): 330.0 [M–H]⁻.

Example 45

4-Chloro-N-[4,4,4-trifluoro-1-hydroxymethyl-2-(2,2,2-trifluoro-ethyl)-butyl]-benzenesulfonamide

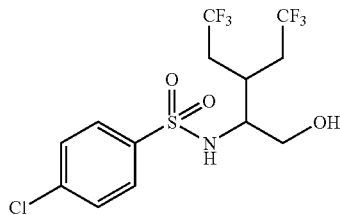

A. 4-Methyl-N-[4,4,4-trifluoro-2-(2,2,2-trifluoroethyl)butylidene]benzenesulfinamide To the crude organic extract of 4,4,4-trifluoro-2-(2,2,2-trifluoroethyl)butyraldehyde, prepared in Example 2 step F, in $CH_2Cl_2$ (100 mL) was added titanium (IV) isopropoxide (4.5 g, 16 mmol) followed by mixture of (±) -toluene sulfinimide (744 mg, 4.8 mmol) and the solution was heated to reflux for 18 h. The mixture was then cooled and water (20 mL) was added. The suspension was filtered through a pad of the Celite® reagent and the filter cake was washed with $CH_2Cl_2$. The layers of the filtrate were separated. The combined organic extracts were washed with brine, dried over $Na_2SO_4$, filtered, and concentrated. The crude product was purified by Biotage Flash™ chromatography, eluent: 20:80 EtOAc-hexanes, to afford the title compound as a yellow oil (420 mg) in 30% yield. Mass Spectrum (–ESI): 344 [M–H]⁻.

B. 4-Methyl-benzenensulfinic acid [1-cyano-4,4,4,-trifluoro-2-(2,2,2-trifluoroethyl)-butyl]amide To diethylaluminum cyanide (1M in toluene, 1.74 mL, 1.74 mmol) in THF (3 mL) at 0° C. was added isopropyl alcohol (88 µL, 1.16 mmol). After 15 min, this solution was added to a solution of 4-methyl-N-[4,4,4-trifluoro-2-(2,2,2-trifluoroethyl)butylidene]benzenesulfinamide (0.40 g, 1.16 mmol) in THF (25 mL) at 25° C. The solution was kept 25° C. for 2 h. Saturated aqueous $NH_4Cl$ (3 mL) was added and reaction mixture was extracted with EtOAc (3×10 mL). The combined organic layers were washed with brine, dried over $Na_2SO_4$ and evaporated to a crude oil which was purified by flash chromatography 20:80 EtOAc:hexanes to provide a clear oil (259 mg) in 60% yield. Mass Spectrum (–ESI): 371 [M–H]⁻.

C. 2-Amino-5,5,5-trifluoro-3-(2,2,2-trifluoroethyl)-pentanoic acid methyl ester A solution of 4-methyl-benzenensulfinic acid [1-cyano-4,4,4,-trifluoro-2-(2,2,2-trifluoroethyl)-butyl]amide (0.25 g, 0.67 mmol) in concentrated HCl (5 mL) was heated to 100° C. for 19 h. The solvent was removed in vacuo and azeotroped with toluene (2×5 mL). The crude solid was taken up in anhydrous methanol (5 mL) and acetyl chloride (0.50 mL) was carefully added and the reaction was heated to reflux for 18 h. The solvent was removed in vacuo to afford a crude product which was partitioned between EtOAc and 2M HCl. The aqueous layer was extracted with EtOAc. The aqueous layer was then treated with sat. NaHCO$_3$ until pH>10 and extracted with EtOAc (3×10 mL). The organic layer was dried over Na$_2$SO$_4$ and evaporated leaving an oil (108 mg) in 61% yield. Mass Spectrum (+ESI): 268 [M+H]$^+$.

D. 2-(4-Chloro-benzenesulfonylamino)-5,5,5-trifluoro-3-(2,2,2-trifluoroethyl)-pentanoic acid methyl ester 4-Chlorophenyl sulphonyl chloride (85 mg, 0.40 mmol) was added to a solution of 2-amino-5,5,5-trifluoro-3-(2,2,2-trifluoroethyl)-pentanoic acid methyl ester (108 mg, 0.40 mmol) and pyridine (0.15 mL, 1.00 mmol) in CH$_2$Cl$_2$ (2 mL) and the reaction was subsequently stirred for 18 hours at 25° C. The solvent was removed in vacuo and the residue was dissolved in EtOAc (20 mL). This solution was washed with 1M HCl (2×10 mL) and brine (10 mL), dried over Na$_2$SO$_4$ and evaporated to afford a crude oil which was purified by flash chromatography, eluting with 20:80 EtOAc:hexanes, to provide the title compound (125 mg) as an oil in 70% yield. Mass Spectrum (−ESI): 446.0 [M−H]$^-$.

E. 4-Chloro-N-[4,4,4-trifluoro-1-hydroxymethyl-2-(2,2,2-trifluoroethyl)-butyl]-benzenesulfonamide A solution of 2-(4-chloro-benzenesulfonylamino)-5,5,5-trifluoro-3-(2,2,2-trifluoroethyl)-pentanoic acid methyl ester (120 mg, 0.27 mmol) in THF (5 mL) was treated with LiBH$_4$ (2M THF, 0.3 mL) for 18 hours at 25° C. The reaction was carefully quenched by the addition of 2M HCl and the organic solvent removed in vacuo. The aqueous layer was extracted with EtOAc (2×10 mL). The organic layers were combined, dried over Na$_2$SO$_4$ and evaporated to afford a crude oil which was purified by flash chromatography, eluting with 30:70 EtOAc:hexanes, to provide the title compound as a white solid (75 mg) in 67% yield. Mass Spectrum (−ESI): 412.0 (M−H)$^-$.

Example 46

3,4-Dichloro-N-[(1S,2S)-3,3,3-trifluoro-1-(hydroxymethyl)-2-methylpropyl]benzenesulfonamide

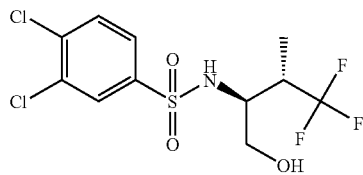

A. (4S)-4-Benzyl-3-[(3S)-3-(4,4,4-trifluoromethyl)butanoyl]-1,3-oxazolidin-2-one To a cooled (−78° C.) solution of 4,4,4-trifluoro-3-methyl-butyric acid (75 mmol, 11.7 g) in THF (750 mL) was added TEA (112.5 mmol, 11.4 g, 15.7 mL) followed by pivaloyl chloride (82.5 mmol, 9.95 g, 10.1 mL). The reaction was stirred for 75 min, was allowed to warm up to −5° C. over 5 min, and held at that temperature for 25 min. In a separate flask, a solution of (S)-(−)-4-benzyl-1,3-oxazolidin-2-one (157.5 mmol, 27.9 g) in THF (300 mL) was cooled to −78° C. and n-BuLi (1.64M in hexanes, 150 mL, 91.5 mmol) was added. After the addition was complete, the solution was stirred for 30 min after which this solution was cooled to −78° C. and was added via cannula to the suspension of mixed anhydride. The reaction mixture was allowed to warm overnight. 1N sodium bisulfate was added to the reaction mixture. The THF was removed in vacuo. The resulting aqueous layer was extracted with dichloromethane (DCM) and the combined organic layers were washed with saturated NaHCO$_3$, dried over Na$_2$SO$_4$, filtered, and concentrated in vacuo to give 42 g of a light yellow viscous oil. Flash chromatography (gradient EtOAc/hexanes) gave 24 g of a viscous oil. The oil was washed twice with NaHCO$_3$, dried over Na$_2$SO$_4$, filtered, and concentrated in vacuo to give 21 g of a viscous oil. Flash chromatography on SiO$_2$ (gradient Et$_2$O/hexanes) provided the title compound (3.79 g, 16%) as a white solid. MS (+ESI) 316.1 m/z ([M+H]$^+$).

B. (4S)-4-Benzyl-3-[((2S,3S)-2-azido-3-(4,4,4-trifluoromethyl)butanoyl]-1,3-oxazolidin-2-one A solution, cooled to −78° C., of lithium diisopropyl amide, prepared fresh from n-BuLi (1.64M in hexanes, 13.2 mmol) and diisopropyl amine (1.3 g, 13.2 mmol) in THF (40 mL), was added via cannula to a precooled (−78° C.) solution of (4S)-4-benzyl-3-[(3S)-3-(4,4,4-trifluoromethyl)butanoyl]-1,3-oxazolidin-2-one (3.79 g, 12.0 mmol) in THF (40 mL). The reaction mixture was stirred at −78° C. for 0.5 hours after which a −78° C. solution of trisyl azide (4.09 g, 13.2 mmol) in THF (40 mL) was added rapidly via cannula. After 3 min, AcOH (55.2 mmol, 3.17 mL) was added to the reaction mixture. The cooling bath was removed and the reaction mixture was allowed to stir at room temperature overnight. The reaction mixture was diluted with saturated NaCl and the mixture was stirred for 30 seconds. The mixture was extracted with CH$_2$Cl$_2$. The combined organic layers were dried over Na$_2$SO$_4$, filtered, and concentrated in vacuo to provide a yellow oil. Flash chromatography on SiO$_2$ (gradient EtOAc/hexanes) provided the title compound (3.48 g, 81%) as a light yellow viscous oil. MS (+ESI) m/z 331.1 [M+H]$^+$

C. (4S)-4-Benzyl-3-[(2S,3S)-2-amino-3-(4,4,4-trifluoromethyl)butanoyl]-1,3-oxazolidin-2-one hydrochloride Methanolic HCl was prepared from MeOH (20 mL) and propionyl chloride (19.08 mmol, 1.77 g, 1.66 mL) at room temperature. A solution of (4S)-4-benzyl-3-[((2S,3S)-2-azido-3-(4,4,4-trifluoromethyl)butanoyl]-1,3-oxazolidin-2-one (9.54 mmol, 3.4 g) in MeOH (75 mL) was added to the methanolic HCl solution and the reaction mixture was hydrogenated at 1 atm over 10% Pd/C (500 mg) overnight. The reaction was filtered through the Celite® reagent with MeOH. The solution was concentrated in vacuo to yield a yellow solid. MeOH was added (<5 mL) followed by Et$_2$O. The mixture was stirred for at least 30 min, filtered off, washed with Et₂O, and dried under vacuum to provide the title compound as a white solid (2.58 g, 73%). MS (+ESI) m/z 331.1 [M+H]⁺

D. (4S)-4-Benzyl-3-[(2S,3S)-2-{N-(3,4-dichlorophenylsulfonyl)}-3-(4,4,4-trifluoromethyl)butanoyl]-1,3-oxazolidin-2-one A solution of DMAP (0.945 mmol, 115 mg) and 3,4-dichlorophenylsulfonyl chloride (0.9 mmol, 221 mg, 141 μL) in DCM (5 mL) was stirred for 15 min. To this suspension was slowly added a cloudy solution of (4S)-4-benzyl-3-[(2S,3S)-2-amino-3-(4,4,4-trifluoromethyl)butanoyl]-1,3-oxazolidin-2-one hydrochloride (0.45 mmol, 168 mg) in DCM (750 μL). The reaction mixture was stirred at room temperature for 48 h. The reaction mixture was diluted with DCM and washed with water. The organic layer was dried over Na₂SO₄, filtered, and concentrated in vacuo. Flash chromatography on SiO₂ (gradient EtOAc/hexanes) provided the title compound as a white powder (208 mg, 86%). ¹H NMR 500 MHz (DMSO-d₆) δ 0.98 (d, J=7.07 Hz, 3H); 2.40-2.50 (m, 2H); 3.00-3.10 (m, 1H); 4.06 (dd, J=8.58 Hz, 2.55 Hz, 1H); 4.26 (t, J=8.12 Hz, 1H); 4.35-4.42 (m, 1H); 5.65 (dd, J=10.6 Hz, 2.26 Hz, 1H); 7.01 (d, J=6.61 Hz, 2H); 7.20-7.30 (m, 3H); 7.19-7.31 (m, 4H); 7.74 (dd, J=8.42 Hz, 2.15 Hz, 1H); 7.88 (d, J=8.35 Hz, 1H); 7.96 (d, J=2.2 Hz, 1H); 8.90 (d, J=10.7 Hz, 1H).

E. 3,4-Dichloro-N-[(1S,2S)-3,3,3-trifluoro-1-(hydroxymethyl)-2-methylpropyl]benzenesulfonamide To a solution of (4S)-4-benzyl-3-[(2S,3S)-2-{N-(3,4-dichlorophenylsulfonyl)}-3-(4,4,4-trifluoromethyl)butanoyl]-1,3-oxazolidin-2-one (0.380 mmol, 205 mg) in dry THF (2 mL) was added LiBH₄ (2.0M in THF, 0.762 mmol, 381 μL) dropwise at room temperature. The reaction mixture was stirred at room temperature for 2 h. 2N HCl was added carefully until no more foam appeared. The reaction mixture was diluted with water and partitioned with EtOAc. The organic layer was separated and the aqueous layer was extracted with EtOAc. The combined organic layers were dried over Na₂SO₄, filtered, and concentrated in vacuo to give an oil. Flash chromatography on SiO₂ (gradient EtOAc/hexanes) provided the title compound as a white solid (88.8 mg, 63%). MS (-ESI) m/z 364 ([M-H]⁻)

Example 47

N-[(1S,2S)-3,3,3-Trifluoro-1-(hydroxymethyl)-2-methylpropyl]-4-(trifluoromethyl)benzenesulfonamide

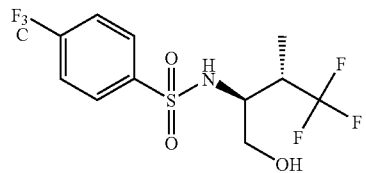

A. (4S)-4-Benzyl-3-[(2S,3S)-2-{N-(4-(trifluoromethyl)benzenesulfonyl)}-3-(4,4,4-trifluoromethyl)butanoyl]-1,3-oxazolidin-2-one The title compound was prepared in a similar fashion as step D of Example 46 using (4S)-4-benzyl-3-[(2S,3S)-2-amino-3-(4,4,4-trifluoromethyl)butanoyl]-1,3-oxazolidin-2-one hydrochloride (0.45 mmol, 168 mg) from step C of Example 46, DMAP (0.945 mmol, 115 mg), and 4-(trifluoromethyl)benzenesulfonyl chloride (0.9 mmol, 220 mg) in DCM (5 mL total volume). ¹H NMR 500 MHz (DMSO-d₆) δ 1.00 (d, J=7.08 Hz, 3H); 2.36 (d, J=6.03 Hz, 2H); 2.98-3.10 (m, 1H); 4.01-4.05 (m, 1H); 4.23 (t, J=8.24 Hz, 1H); 4.30-4.37 (m, 1H); 5.68 (dd, J=10.6 Hz, 2.50 Hz, 1H); 6.99 (d, J=6.73 Hz, 2H); 7.19-7.30 (m, 3H); 7.98 (quart, J=7.81 Hz, 4H); 8.87 (d, J=10.7 Hz, 1H).

B. N-[(1S,2S)-3,3,3-Trifluoro-1-(hydroxymethyl)-2-methylpropyl]-4-(trifluoromethyl)benzenesulfonamide The title compound was prepared in a similar fashion to step E of Example 46 as a white solid (28.2 mg, 45%) using (4S)-4-benzyl-3-[(2S,3S)-2-{N-(4-(trifluoromethyl)benzenesulfonyl)}-3-(4,4,4-trifluoromethyl)butanoyl]-1,3-oxazolidin-2-one (0.265 mmol, 130 mg) from step A of Example 47 and LiBH₄ (2.0M in THF, 0.380 mmol, 190 μL) in THF (2.7 mL total volume). MS (-ES) m/z 364.1 ([M-H]⁻)

Example 48

4-Fluoro-N-[(1S,2S)-3,3,3-trifluoro-1-(hydroxymethyl)-2-methylpropyl]benzenesulfonamide

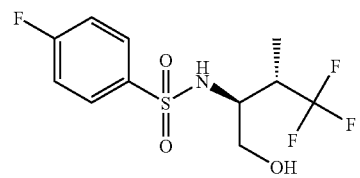

A. (4S)-4-Benzyl-3-[(2S,3 S)-2-{N-(4-fluorophenylsulfonyl)}-3-(4,4,4-trifluoromethyl)butanoyl]-1,3-oxazolidin-2-one The title compound was prepared in a similar fashion to step D of Example 46 using (4S)-4-benzyl-3-[(2S,3S)-2-amino-3-(4,4,4-trifluoromethyl)butanoyl]-1,3-oxazolidin-2-one hydrochloride (0.30 mmol, 113 mg) from step C of Example 46, DMAP (0.63 mmol, 77 mg), and 4-fluorophenylsulfonyl chloride (0.9 mmol, 220 mg) in DCM (1.7 mL total volume).

¹H NMR 500 MHz (DMSO-d₆) δ 1.00 (d, J=7.08 Hz, 3 H); 2.45-2.50 (m, 2H); 2.95-3.05 (m, 1H); 4.05 (dd, J=8.65 Hz, 2.38 Hz, 1H); 4.25 (t, J=8.30 Hz, 1H); 4.36-4.40 (m, 1H); 5.64 (dd, J=10.7 Hz, 2.49 Hz, 1H); 7.02 (d, J=6.73 Hz, 2H); 7.20-7.30 (m, 3H); 7.42 (t, J=8.88 Hz, 3H); 7.81-7.85 (m, 2H); 8.64 (d, J=10.7 Hz, 1H)

B. 4-Fluoro-N-[(1S,2S)-3,3,3-trifluoro-1-(hydroxymethyl)-2-methylpropyl]benzenesulfonamide The title compound was prepared in a similar fashion to step E of Example 46 as a white solid (58 mg, 85%) using (4S)-4-benzyl-3-[(2S,3S)-2-{N-(4-fluorophenylsulfonyl)}-3-(4,4,4-trifluoromethyl)butanoyl]-1,3-oxazolidin-2-one (0.215 mmol, 105 mg) from step A of Example 48 and LiBH₄ (2.0M in THF, 0.430 mmol, 215 μL) in THF (1.4 mL total volume). MS (ES) m/z 314.1 ([M-H]⁻)

Example 49

Pharmacology: Aβ40/42 ELISA Assay

Compounds are diluted from DMSO stocks to 2 μM and below in a cell culture medium. Compounds are then applied to CHO cells carrying the APP-REP-NL plasmid [Sudhir et. al, J. Biol. Chem. 267:25602-25608 (1992)] for a period of 22 hours. After the conditioning period, medium is collected, diluted in assay buffer containing protein, and samples, controls, and synthetic peptide standards are incubated on a prepared ELISA plate. Using a sandwich ELISA with antibodies specifically directed against the carboxyl terminus of beta amyloid 40 or 42 [analogous to the method reported by Haugabook et al., J. Neurosci. Methods 108:171-179 (2001) but using goat anti-mouse IgGl (source: Southern Biotech) as the anchor, 6E10 as the capture antibody (Source: SENETEK), rabbit antiαβ40 and antiαβB42 (source: QCB) and APL-donkey anti-rabbit IgG (H+L, source: Southern Biotech) as the detection antibody], the effect of the compound treatment on the cellular production of extracellular beta amyloid is quantified. Cells treated with compound are subsequently incubated in cell culture medium containing MTS-formazan. After a short incubation period, MTS/medium containing plates are read in a spectrophotometer to determine the extent to which compound toxicity affected the cell's metabolism and ability to synthesize beta amyloid.

A. Materials for the Assay:

Test Samples: compound samples are supplied as 20 mM stock solutions in a 100% DMSO solution.

APP-REP-NL cells: Qualified cell lines are carried from week to week using 1:100 dilutions and are cultured in DMEM supplemented with 1× antibiotic/antimycotic, 200 μg/ml of G418 antibiotic, and 10% certified fetal calf serum. Cells are also banked in liquid nitrogen. Periodically, beta amyloid production is assessed, and cells are either kept in culture or replaced with progenitors at full expression.

Antibodies: Are from certified lots that have already been qualified in this assay. Antibodies are stored in small frozen aliquots at −80° C. that are thawed and used.

B. Criteria for Activity

A compound is considered active if it has an $EC_{50}$ for Aβ 40 reduction of <100 μM and no toxicity at doses in the vicinity the $EC_{50}$.

| Ex # | ELISA Data $EC_{50}$ A$\beta_{40}$ (nM) | ELISA Data $EC_{50}$ A$\beta_{42}$ (nM) | Name |
|---|---|---|---|
| 1 | 220 | 177 | 4-chloro-N-[(1S)-3,3,3-trifluoro-1-(hydroxymethyl)-2-(trifluoromethyl)propyl]benzenesulfonamide |
| 2 | 334 | 204 | 4-chloro-N-[(1S)-4,4,4-trifluoro-1-(hydroxymethyl)-2-(2,2,2-trifluoroethyl)butyl]benzenesulfonamide |
| 3 | 9935 | 13847 | 4-chloro-3-methoxy-N-[3,3,3-trifluoro-1-(hydroxymethyl)-2-(trifluoromethyl)propyl]benzenesulfonamide |
| 4 | 37687 | 89862 | 4-chloro-N-[3,3,3-trifluoro-1-(hydroxymethyl)-2-(trifluoromethyl)propyl]-3-(trifluoromethyl)benzenesulfonamide |
| 5 | 45973 | 76938 | 4-chloro-3-nitro-N-[3,3,3-trifluoro-1-(hydroxymethyl)-2-(trifluoromethyl)propyl]benzenesulfonamide |
| 6 | 13432 | 11220 | 3-acetyl-N-[3,3,3-trifluoro-1-(hydroxymethyl)-2-(trifluoromethyl)propyl]benzenesulfonamide |
| 7 | 4461 | 4023 | 4-(difluoromethoxy)-N-[3,3,3-trifluoro-1-(hydroxymethyl)-2-(trifluoromethyl)propyl]benzenesulfonamide |
| 8 | 47937 | | 3-(difluoromethoxy)-N-[3,3,3-trifluoro-1-(hydroxymethyl) 2-(trifluoromethyl)propyl]benzenesulfonamide |
| 9 | 7201 | 6751 | 4-ethyl-N-[3,3,3-trifluoro-1-(hydroxymethyl)-2-(trifluoromethyl)propyl]benzenesulfonamide |
| 10 | 17718 | 44104 | 4-isopropyl-N-[3,3,3-trifluoro-1-(hydroxymethyl)-2-(trifluoromethyl)propyl]benzenesulfonamide |
| 11 | 6807 | 6441 | 4-methoxy-N-[3,3,3-trifluoro-1-(hydroxymethyl)-2-(trifluoromethyl)propyl]benzenesulfonamide |
| 12 | 24102 | | 3-methoxy-N-[3,3,3-trifluoro-1-(hydroxymethyl)-2-(trifluoromethyl)propyl]benzenesulfonamide |
| 13 | 17993 | | 4-propyl-N-[3,3,3-trifluoro-1-(hydroxymethyl)-2-(trifluoromethyl)propyl]benzenesulfonamide |
| 14 | 1504 | 1261 | 4-methyl-N-[3,3,3-trifluoro-1-(hydroxymethyl)-2-(trifluoromethyl)propyl]benzenesulfonamide |
| 15 | 15068 | 14546 | 3-methyl-N-[3,3,3-trifluoro-1-(hydroxymethyl)-2-(trifluoromethyl)propyl]benzenesulfonamide |
| 16 | 28119 | | N-[3,3,3-trifluoro-1-(hydroxymethyl)-2-(trifluoromethyl)propyl]-3-(trifluoromethyl)benzenesulfonamide |
| 17 | 2287 | 1936 | N-[3,3,3-trifluoro-1-(hydroxymethyl)-2-(trifluoromethyl)propyl]-4-(trifluoromethyl)benzenesulfonamide |
| 18 | 90678 | 100780 | 4-cyano-N-(3,3,3-trifluoro-1-hydroxymethyl-2-trifluoromethyl-propyl)-benzenesulfonamide |
| 19 | 27804 | 26845 | 4-nitro-N-(3,3,3-trifluoro-1-hydroxymethyl-2-trifluoromethyl-propyl)-benzenesulfonamide |
| 20 | 8508 | 6417 | N-(3,3,3-trifluoro-1-hydroxymethyl-2-trifluoromethyl-propyl)-4-trifluoromethoxy-benzenesulfonamide |
| 21 | 997 | 932 | 4-chloro-N-(3,3,3-trifluoro-1-hydroxymethyl-2-trifluoromethyl-propyl)-benzenesulfonamide |

-continued

| Ex # | ELISA Data EC$_{50}$ Aβ$_{40}$ (nM) | ELISA Data EC$_{50}$ Aβ$_{42}$ (nM) | Name |
|---|---|---|---|
| 22 | 5716 | 6336 | 3,5-difluoro-N-[3,3,3-trifluoro-1-(hydroxymethyl)-2-(trifluoromethyl)propyl]benzenesulfonamide |
| 23 | 22315 | | 4-chloro-3-(methylthio)-N-[3,3,3-trifluoro-1-(hydroxymethyl)-2-(trifluoromethyl)propyl]benzenesulfonamide |
| 24 | 1091 | 1141 | 4-chloro-3-fluoro-N-[3,3,3-trifluoro-1-(hydroxymethyl)-2-(trifluoromethyl)propyl]benzenesulfonamide |
| 25 | 6635 | 8369 | 4-fluoro-3-methyl-N-[3,3,3-trifluoro-1-(hydroxymethyl)-2-(trifluoromethyl)propyl]benzenesulfonamide |
| 26 | 1130 | 1207 | 4-fluoro-N-(3,3,3-trifluoro-1-hydroxymethyl-2-trifluoromethyl-propyl)-benzenesulfonamide |
| 27 | 9077 | 12069 | 3-fluoro-N-(3,3,3-trifluoro-1-hydroxymethyl-2-trifluoromethyl-propyl)-benzenesulfonamide |
| 28 | 23380 | 44245 | 2-fluoro-N-(3,3,3-trifluoro-1-hydroxymethyl-2-trifluoromethyl-propyl)-benzenesulfonamide |
| 29 | 24218 | 37184 | 3-chloro-N-(3,3,3-trifluoro-1-hydroxymethyl-2-trifluoromethyl-propyl)-benzenesulfonamide |
| 30 | 25438 | 24472 | 2-chloro-N-(3,3,3-trifluoro-1-hydroxymethyl-2-trifluoromethyl-propyl)-benzenesulfonamide |
| 31 | 886 | 905 | 4-bromo-N-(3,3,3-trifluoro-1-hydroxymethyl-2-trifluoromethyl-propyl)-benzenesulfonamide |
| 32 | 19844 | 25335 | 3-bromo-N-(3,3,3-trifluoro-1-hydroxymethyl-2-trifluoromethyl-propyl)-benzenesulfonamide |
| 33 | 6261 | 7021 | N-(3,3,3-trifluoro-1-hydroxymethyl-2-trifluoromethyl-propyl)-benzenesulfonamide |
| 34 | 2224 | 2402 | 3,4-difluoro-N-(3,3,3-trifluoro-1-hydroxymethyl-2-trifluoromethyl-propyl)-benzenesulfonamide |
| 35 | 9766 | 11170 | 2,4-difluoro-N-(3,3,3-trifluoro-1-hydroxymethyl-2-trifluoromethyl-propyl)-benzenesulfonamide |
| 36 | 63950 | | 3,5-dichloro-N-(3,3,3-trifluoro-1-hydroxymethyl-2-trifluoromethyl-propyl)-benzenesulfonamide |
| 37 | 11091 | 14002 | 2,3-dichloro-N-(3,3,3-trifluoro-1-hydroxymethyl-2-trifluoromethyl-propyl)-benzenesulfonamide |
| 38 | 4681 | 6551 | 3,4-dichloro-N-(3,3,3-trifluoro-1-hydroxymethyl-2-trifluoromethyl-propyl)-benzenesulfonamide |
| 39 | 6716 | 8625 | 3-chloro-4-fluoro-N-[3,3,3-trifluoro-1-(hydroxymethyl)-2-(trifluoromethyl)propyl]benzenesulfonamide |
| 40 | 32168 | 45374 | 2,3,4-trifluoro-N-(3,3,3-trifluoro-1-hydroxymethyl-2-trifluoromethyl-propyl)-benzenesulfonamide |
| 41 | 5573 | 5369 | 3,4-dichloro-N-[(1S)-3,3,3-trifluoro-1-(hydroxymethyl)-2-(trifluoromethyl)propyl]benzenesulfonamide |
| 42 | 6632 | 5503 | 3,4,5-trifluoro-N-[3,3,3-trifluoro-1-(hydroxymethyl)-2-(trifluoromethyl)propyl]benzenesulfonamide |
| 43 | 423 | 384 | 4-chloro-N-[(1S,2S)-3,3,3-trifluoro-1-(hydroxymethyl)-2-methylpropyl]benzenesulfonamide |
| 44 | 2942 | 3514 | 4-chloro-N-[(1S,2R)-3,3,3-trifluoro-1-(hydroxymethyl)-2-methylpropyl]benzenesulfonamide |
| 45 | 518 | 504 | 4-chloro-N-[4,4,4-trifluoro-1-hydroxymethyl-2-(2,2,2-trifluoro-ethyl)-butyl]-benzenesulfonamide |
| 46 | 5070 | 4836 | 3,4-dichloro-N-[(1S,2S)-3,3,3-trifluoro-1-(hydroxymethyl)-2-methylpropyl]benzenesulfonamide |
| 47 | 1402 | 1171 | N-[(1S,2S)-3,3,3-trifluoro-1-(hydroxymethyl)-2-methylpropyl]-4-(trifluoromethyl)benzenesulfonamide |
| 48 | 651 | 563 | 4-fluoro-N-[(1S,2S)-3,3,3-trifluoro-1-(hydroxymethyl)-2-methylpropyl]benzenesulfonamide |

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A compound of Formula (I), or pharmaceutically acceptable salts and/or hydrates thereof, wherein Formula (I) has the structure:

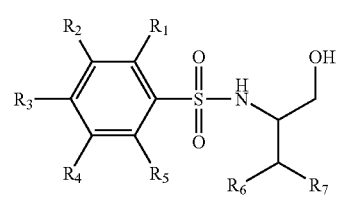

wherein:
R₁ through R₅ are independently selected from the group consisting of H, halogen, lower alkyl, lower alkoxy, $OCF_3$, $OCF_2H$, $CF_3$, $NO_2$, CN, $CH_3CO$, and $SCH_3$;
R₆ and R₇ are independently selected from the group consisting of lower alkyl and $CF_3(CH_2)_n$; and
n is independently selected from the group consisting of 0, 1, 2 and 3, provided that at least one of R₆ and R₇ are $CF_3(CH_2)_n$.

2. The compound according to claim 1, wherein one of R₆ or R₇ is $CF_3(CH_2)_n$ and the other is $CH_3$.

3. The compound according to claim 1, selected from the group consisting of:
 4-chloro-N-[(1S,2S)-3,3,3-trifluoro-1-(hydroxymethyl)-2-methyipropyl]benzenesulfonamide;
 4-chloro-N-[(1S,2R)-3,3,3-trifluoro-1-(hydroxymethyl)-2-methylpropyl]benzenesulfonamide;
 3,4-dichloro-N-[(1S,2S)-3,3,3-trifluoro-1-(hydroxymethyl)-2-methylpropyl]benzenesulfonamide;
 4-fluoro-N-[(1S,2S)-3,3,3-trifluoro-1-(hydroxymethyl)-2-methylpropyl]benzenesulfonamide; and N-[(1S,2S)-3,3,3-trifluoro-1-(hydroxymethyl)-2-methylpropyl]-4-(trifluoromethyl)benzenesulfonamide.

4. The compound according to claim 1, wherein R₃ is halogen.

5. The compound according to claim 1, wherein R₃ is $CF_3$.

6. The compound according to claim 1, wherein one of R₆ or R₇ is $CF_3(CH_2)_n$ where n is 1, 2 or 3 and the other is selected from lower alkyl and $CF_3(CH_2)_n$, wherein n is 2 or 3.

7. The compound according to claim 1, wherein the compound has a chiral center at the C attached to the N and said compound has S-stereochemistry at the chiral center.

8. The compound according to claim 1, wherein R₁, R₂, R₄, and R₅ are H.

9. The compound according to claim 1, wherein R₆ and R₇ are $CF_3(CH_2)_n$ and n is 0.

10. The compound according to claim 1, wherein the compound is selected from the group consisting of:
 4-chloro-N-[(1S)-3,3,3-trifluoro-1-(hydroxymethyl)-2-(trifluoromethyl)propyl]benzenesulfonamide;
 4-chloro-N-[(1S)-4,4,4-trifluoro-1-(hydroxymethyl)-2-(2,2,2-trifluoromethyl)butyl]benzenesulfonamide;
 4-chloro-3-methoxy-N-[3,3,3-trifluoro-1-(hydroxymethyl)-2-(trifluoromethyl)propyl]benzenesulfonamide;
 4-chloro-N-[3,3,3-trifluoro-1-(hydroxymethyl)-2-(trifluoromethyl) propyl]-3-(trifluoromethyl)benzenesulfonamide;
 4-chloro-3-nitro-N-[3,3,3-trifluoro-1-(hydroxymethyl)-2-(trifluoromethyl)propyl]benzenesulfonamide;
 3-acetyl-N-[3,3,3-trifluoro-1-(hydroxymethyl)-2-(trifluoromethyl)propyl]benzenesulfonamide;
 4-(difluoromethoxy)-N-[3,3,3-trifluoro-1-(hydroxymethyl)-2-(trifluoromethyl)propyl]benzenesulfonamide;
 3-(difluoromethoxy)-N-[3,3,3-trifluoro-1-(hydroxymethyl)-2-(trifluoromethyl)propyl]benzenesulfonamide;
 4-ethyl-N-[3,3,3-trifluoro-1-(hydroxymethyl)-2-(trifluoromethyl)propyl]benzenesulfonamide;
 4-isopropyl-N-[3,3,3-trifluoro-1-(hydroxymethyl)-2-(trifluoromethyl)propyl]benzenesulfonamide;
 4-methoxy-N-[3,3,3-trifluoro-1-(hydroxymethyl)-2-(trifluoromethyl)propyl]benzenesulfonamide;
 3-methoxy-N-[3,3,3-trifluoro-1-(hydroxymethyl)-2-(trifluoromethyl)propyl]benzenesulfonamide;
 4-propyl-N-[3,3,3-trifluoro-1-(hydroxymethyl)-2-(trifluoromethyl)propyl]benzenesulfonamide;
 4-methyl-N-[3,3,3-trifluoro-1-(hydroxymethyl)-2-(trifluoromethyl)propyl]benzenesulfonamide;
 3-methyl-N-[3,3,3-trifluoro-1-(hydroxymethyl)-2-(trifluoromethyl)propyl]benzenesulfonamide;
 N-[3,3,3-trifluoro-1-(hydroxymethyl)-2-(trifluoromethyl)propyl]-3-(trifluoromethyl)benzenesulfonamide;
 N-[3,3,3-trifluoro-1-(hydroxymethyl)-2-(trifluoromethyl)propyl]-4-(trifluoromethyl)benzenesulfonamide;
 4-cyano-N-(3,3,3-trifluoro-1-hydroxymethyl-2-trifluoromethyl-propyl)-benzenesulfonamide;
 4-nitro-N-(3,3,3-trifluoro-1-hydroxymethyl-2-trifluoromethyl-propyl)-benzenesulfonamide;
 N-(3,3,3-trifluoro-1-hydroxymethyl-2-trifluoromethyl-propyl)-4-trifluoromethoxy-benzenesulfonamide;
 4-chloro-N-(3,3,3-trifluoro-1-hydroxymethyl-2-trifluoromethyl-propyl)-benzenesulfonamide;
 3,5-difluoro-N-[3,3,3-trifluoro-1-(hydroxymethyl)-2-(trifluoromethyl)propyl]benzenesulfonamide;
 4-chloro-3-(methylthio)-N-[3,3,3-trifluoro-1-(hydroxymethyl)-2-(trifluoromethyl)propyl]benzenesulfonamide;
 4-chloro-3-fluoro-N-[3,3,3-trifluoro-1-(hydroxymethyl)-2-(trifluoromethyl)propyl]benzenesulfonamide;
 4-fluoro-3-methyl-N-[3,3,3-trifluoro-1-(hydroxymethyl)-2-(trifluoromethyl)propyl]benzenesulfonamide;
 4-fluoro-N-(3,3,3-trifluoro-1-hydroxymethyl-2-trifluoromethyl-propyl)-benzenesulfonamide;
 3-fluoro-N-(3,3,3-trifluoro-1-hydroxymethyl-2-trifluoromethyl-propyl)-benzenesulfonamide;
 2-fluoro-N-(3,3,3-trifluoro-1-hydroxymethyl-2-trifluoromethyl-propyl)-benzenesulfonamide;
 3-chloro-N-(3,3,3-trifluoro-1-hydroxymethyl-2-trifluoromethyl-propyl)-benzenesulfonamide;
 2-chloro-N-(3,3,3-trifluoro-1-hydroxymethyl-2-trifluoromethyl-propyl)-benzenesulfonamide;
 4-bromo-N-(3,3,3-trifluoro-1-hydroxymethyl-2-trifluoromethyl-propyl)-benzenesulfonamide;
 3-bromo-N-(3,3,3-trifluoro-1-hydroxymethyl-2-trifluoromethyl-propyl)-benzenesulfonamide;
 N-(3,3,3-trifluoro-1-hydroxymethyl-2-trifluoromethyl-propyl)-benzenesulfonamide;
 3,4-difluoro-N-(3,3,3-trifluoro-1-hydroxymethyl-2-trifluoromethyl-propyl)-benzenesulfonamide;
 2,4-difluoro-N-(3,3,3-trifluoro-1-hydroxymethyl-2-trifluoromethyl-propyl)-benzenesulfonamide;
 3,5-dichloro-N-(3,3,3-trifluoro-1-hydroxymethyl-2-trifluoromethyl-propyl)-benzenesulfonamide;
 2,3-dichloro-N-(3,3,3-trifluoro-1-hydroxymethyl-2-trifluoromethyl-propyl)-benzenesulfonamide;
 3,4-dichloro-N-(3,3,3-trifluoro-1-hydroxymethyl-2-trifluoromethyl-propyl)-benzenesulfonamide;
 3-chloro-4-fluoro-N-[3,3,3-trifluoro-1-(hydroxymethyl)-2-(trifluoromethyl)propyl]benzenesulfonamide;
 2,3,4-trifluoro-N-(3,3,3-trifluoro-1-hydroxymethyl-2-trifluoromethyl-propyl)-benzenesulfonamide;
 3,4-dichloro-N-[(1S)-3,3,3-trifluoro-1-(hydroxymethyl)-2-(trifluoromethyl)propyl]benzenesulfonamide;
 4-chloro-N-[4,4,4-trifluoro-1-hydroxymethyl-2-(2,2,2-trifluoro-ethyl)-butyl]-benzenesulfonamide; and
 3,4,5-trifluoro-N-[3,3,3-trifluoro-1-(hydroxymethyl)-2-(trifluoromethyl)propyl]benzenesulfonamide.

11. The compound according to claim 1, wherein the pharmaceutically acceptable salt is selected from the group consisting of salts of bases.

12. The compound according to claim 11, wherein the salts of bases are selected from the group consisting of sodium hydroxide, lithium hydroxide and potassium hydroxide, and mixtures thereof.

13. A pharmaceutical composition comprising a compound of claim 1 and a physiologically compatible carrier.

* * * * *